(12) United States Patent
Angell et al.

(10) Patent No.: US 10,497,970 B2
(45) Date of Patent: Dec. 3, 2019

(54) ALKALI ION CONDUCTING PLASTIC CRYSTALS

(71) Applicants: Charles Austen Angell, Mesa, AZ (US); Iolanda Santana Klein, Tempe, AZ (US); Telpriore Greg Tucker, Phoenix, AZ (US)

(72) Inventors: Charles Austen Angell, Mesa, AZ (US); Iolanda Santana Klein, Tempe, AZ (US); Telpriore Greg Tucker, Phoenix, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/023,959

(22) Filed: Jun. 29, 2018

(65) Prior Publication Data

US 2019/0020060 A1    Jan. 17, 2019

Related U.S. Application Data

(63) Continuation-in-part of application No. 14/775,215, filed as application No. PCT/US2014/029294 on Mar. 14, 2014.

(Continued)

(51) Int. Cl.
*H01M 10/0561* (2010.01)
*H01M 10/0564* (2010.01)
(Continued)

(52) U.S. Cl.
CPC ... *H01M 10/0564* (2013.01); *H01M 10/0525* (2013.01); *C07F 7/025* (2013.01);
(Continued)

(58) Field of Classification Search
CPC .......... H01M 10/056; H01M 10/0561; H01M 10/0562; H01M 2300/0065; H01M 2300/0068
See application file for complete search history.

(56) References Cited

U.S. PATENT DOCUMENTS 3,459,500 A    8/1969    Segura et al.
4,042,482 A    8/1977    Shannon
(Continued)

FOREIGN PATENT DOCUMENTS

CA    2098870 A1    12/1993
CA    2435218       7/2005
(Continued)

OTHER PUBLICATIONS

Hayamizu, K., Aihara, Y., Nakagawa, H., Nukuda, T. & Price, W. S. Ionic Conduction and Ion Diffusion in Binary Room—Temperature Ionic Liquids Composed of [emim][BF 4 ] and LiBF 4. J. Phys. Chem. B 108, 19527-19532 (2004).
(Continued)

*Primary Examiner* — Jeremiah R Smith
(74) *Attorney, Agent, or Firm* — Fish & Richardson P.C.

(57) ABSTRACT

A solid electrolyte represented by general formula $Li_ySiR_x(MO_4)$, where x is an integer from 1 to 3 inclusive, y=4−x, each R present is independently C1-C3 alkyl or C1-C3 alkoxy, and M is sulfur, selenium, or tellurium. Methods of making the solid electrolyte include combining a phenylsilane and a first acid to yield mixture including benzene and a second acid, and combining at least one of an alkali halide, and alkali amide, and an alkali alkoxide with the second acid to yield a product d represented by general formula $Li_ySiR_x(MO_4)_y$. The second acid may be in the form of a liquid or a solid. The phenylsilane includes at least one C1-C3 alkyl substituent or at least one C1-C3 alkoxy substituent, and the
(Continued)

first acid includes at least one of sulfuric acid, selenic acid, and telluric acid.

19 Claims, 16 Drawing Sheets

Related U.S. Application Data

(60) Provisional application No. 62/526,963, filed on Jun. 29, 2017, provisional application No. 61/782,292, filed on Mar. 14, 2013.

(51) Int. Cl.
*H01M 10/0525* (2010.01)
*C07F 7/02* (2006.01)
*H01M 10/0562* (2010.01)
*H01M 10/056* (2010.01)

(52) U.S. Cl.
CPC ...... *H01M 10/056* (2013.01); *H01M 10/0561* (2013.01); *H01M 10/0562* (2013.01); *H01M 2300/006* (2013.01); *H01M 2300/0065* (2013.01); *H01M 2300/0068* (2013.01); *H01M 2300/0091* (2013.01)

(56) References Cited

U.S. PATENT DOCUMENTS

| | | |
|---|---|---|
| 5,455,211 A | 10/1995 | McMillan et al. |
| 5,484,670 A | 1/1996 | Angell et al. |
| 5,506,073 A | 4/1996 | Angell et al. |
| 5,518,970 A | 5/1996 | McMillan et al. |
| 5,786,110 A | 7/1998 | Angell et al. |
| 5,824,433 A | 10/1998 | Angell et al. |
| 5,849,432 A | 12/1998 | Angell et al. |
| 5,855,809 A | 1/1999 | Angell et al. |
| 5,962,169 A | 10/1999 | Angell et al. |
| 6,136,472 A | 10/2000 | Barker |
| 6,155,057 A | 12/2000 | Angell et al. |
| 6,245,465 B1 | 6/2001 | Angell et al. |
| 6,475,561 B1 | 11/2002 | Schwertfeger et al. |
| 6,913,855 B2 | 7/2005 | Stoker et al. |
| 6,955,867 B1* | 10/2005 | Otsuki ............... H01M 10/052 429/314 |
| 7,012,124 B2 | 3/2006 | Angell et al. |
| 7,504,473 B2 | 3/2009 | Angell et al. |
| 7,527,899 B2 | 5/2009 | Angell et al. |
| 7,833,643 B2 | 11/2010 | Angell et al. |
| 7,833,666 B2 | 11/2010 | Angell et al. |
| 7,867,658 B2 | 1/2011 | Angell et al. |
| 8,273,477 B2 | 9/2012 | Angell et al. |
| 8,338,038 B2 | 12/2012 | Coors et al. |
| 8,784,512 B2 | 7/2014 | Wadley |
| 9,647,288 B2 | 5/2017 | Angell et al. |
| 9,768,462 B2 | 9/2017 | Angell et al. |
| 2003/0008190 A1 | 1/2003 | Chisholm et al. |
| 2004/0053134 A1 | 3/2004 | Ozaki et al. |
| 2004/0241553 A1 | 12/2004 | Abe |
| 2005/0095482 A1 | 5/2005 | Garner |
| 2006/0189776 A1 | 8/2006 | Angell et al. |
| 2007/0003836 A1* | 1/2007 | Suzuki ............... H01M 4/02 429/232 |
| 2008/0226989 A1 | 9/2008 | Angell et al. |
| 2009/0226817 A1 | 9/2009 | Angell et al. |
| 2011/0008677 A1 | 1/2011 | Nakane et al. |
| 2011/0020712 A1 | 1/2011 | Angell et al. |
| 2011/0143212 A1 | 6/2011 | Angell et al. |
| 2011/0171528 A1 | 7/2011 | Oladeji |
| 2012/0107690 A1* | 5/2012 | Wakizaka ............... H01M 4/13 429/217 |
| 2013/0209893 A1 | 8/2013 | Archer |
| 2016/0043431 A1* | 2/2016 | Angell ............... H01M 10/0525 429/323 |
| 2017/0309943 A1 | 10/2017 | Angell et al. |
| 2018/0131027 A1 | 5/2018 | Angell et al. |
| 2018/0309170 A1 | 10/2018 | Angell et al. |

FOREIGN PATENT DOCUMENTS

| | | |
|---|---|---|
| EP | 0576225 B1 | 12/1998 |
| MX | 183199 | 11/1996 |
| WO | 1996039725 A1 | 12/1996 |
| WO | 1997016862 A1 | 5/1997 |
| WO | 1997018159 A1 | 5/1997 |
| WO | 1997018595 A1 | 5/1997 |
| WO | 1999019932 A1 | 4/1999 |
| WO | 2000061698 A1 | 10/2000 |
| WO | 2001096446 A1 | 12/2001 |
| WO | 2001098396 A1 | 12/2001 |
| WO | 2001099209 A2 | 12/2001 |
| WO | 2004114445 A1 | 12/2004 |
| WO | 2006078866 A2 | 7/2006 |
| WO | 2008118210 A2 | 10/2008 |
| WO | 2009015367 A2 | 1/2009 |
| WO | 2009042958 A1 | 4/2009 |
| WO | 2014028894 A1 | 2/2014 |
| WO | 2014153146 A1 | 9/2014 |
| WO | WO2014153146 | 9/2014 |
| WO | 2016044324 A1 | 3/2016 |
| WO | 2016191608 A1 | 12/2016 |

OTHER PUBLICATIONS

Ye, H., Huang, J., Xu, J. J., Khalfan, A. & Greenbaum, S. G. Li Ion Conducting Polymer Gel Electrolytes Based on Ionic Liquid/PVDF-HFP Blends. J. Electrochem. Soc. 154, A1048 (2007).

Seino, Y., Ota, T., Takada, K., Hayashi, A. & Tatsumisago, M. A sulphide lithium super ion conductor is superior to liquid ion conductors for use in rechargeable batteries. Energy Environ. Sci. 7, 627-631 (2014).

Hayashi, A., Minami, K., Ujiie, S. & Tatsumisago, M. Preparation and ionic conductivity of Li7P3S11-z glass-ceramic electrolytes. J. Non. Cryst. Solids 356, 2670-2673 (2010).

Ansari, Y., Tucker, T. G. & Angell, C. A. A novel, easily synthesized, anhydrous derivative of phosphoric acid for use in electrolyte with phosphoric acid-based fuel cells. J. Power Sources 237, 47-51 (2013).

Evans, J., Vincent, C. A & Bruce, P. G. Electrochemical measurement of transference numbers in polymer electrolytes. Polymer (Guildf). 28, 2324-2328 (1987).

Zugmann, S. et al. Measurement of transference numbers for lithium ion electrolytes via four different methods, a comparative study. Electrochim. Acta 56, 3926-3933 (2011).

Hayashi, S. & Hayamizu, K. Chemical Shift Standards in High-Resolution Solid-State NMR (1) 13C, 29Si and 1H Nuclei. Bull. Chem. Soc. Jpn. 64, 685-687 (1991).

Eabom, C. Cleavages of aryl-silicon and related bonds by electrophiles. J. Organomet. Chem. 100, 43-57 (1975).

Bassindale, A. R. & Stout, T. The synthesis of functionalised silyltriflates. J. Organomet. Chem. 271, C1-C3 (1984).

Matyjaszewski, K. & Chen, Y. L. Synthesis and reactions of silanes containing two triflate groups. J. Organomet. Chem. 340, 7-12 (1988).

Stallworth, P. et al. NMR, DSC and high pressure electrical conductivity studies of liquid and hybrid electrolytes. J. Power Sources 81-82, 739-747 (1999).

Kim, S.H. et al. A shape-deformable and thermally stable solid-state electrolyte based on a plastic crystal composite polymer electrolyte for flexible/safer lithium-ion batteries. J. Mater. Chem. A 2, 10854-10861 (2014).

Shekibi, Y., Rüther, T., Huang, J. & Hollenkamp, A. F. Realisation of an all solid state lithium battery using solid high temperature plastic crystal electrolytes exhibiting liquid like conductivity. Phys. Chem. Chem. Phys. 14, 4597 (2012).

Fan, J. & Fedkiw, P. S. Electrochemical impedance spectra of full cells: Relation to capacity and capacity-rate of rechargeable Li cells using LiCoO2, LiMn2O4, and LiNiO2 cathodes. J. Power Sources 72, 165-173 (1998).

(56) References Cited

OTHER PUBLICATIONS

Haile, S. M.; Boysen, D. A.; Chisholm, C. R.; Merle, R. B. Solid acids as fuel cell electrolytes. Nature 2001, 410 (6831), 910.

Haile, S. M.; Chisholm, C. R. I.; Sasaki, K.; Boysen, D. A.; Uda, T. Solid acid proton conductors: from laboratory curiosities to fuel cell electrolytes. Faraday Discuss. 2007, 134, 17.

Ansari Y.; Ueno, K.; Zhao, Z.; Angell, C. A. Anhydrous Superprotonic Polymer by Superacid Protonation of Cross-linked (PNCI2)n. J. Phys. Chem. C 2013, 117, 1548.

Ansari, Y.; Tucker, T. G.; Huang, W.; Klein, I. S.; Lee, S.-Y.; Yarger, J. L.; Angell, C. A. A flexible all-inorganic fuel cell membrane with conductivity above Nafion, and durable operation at 150° C. J. Power Sources 2016, 303, 142.

Flowers, R. H.; Gillespie, R. J.; Robinson, E. A. The Sulphuric Acid Solvent System Part V. Solutions of Some Organosilicon Compounds. Can. J. Chem. 1963, 41 (10), 2464.

Merle, R. B.; Chisholm, C. R. I.; Boysen, D. a.; Haile, S. M. Instability of Sulfate and Selenate Solid Acids in Fuel Cell Environments. Energy and Fuels 2003, 17 (1), 210-215.

Greenwood, N. N.; Thompson, A. J. The Mechanism of Electrical Conduction in Fused Phosphoric and Trideuterophosphoric Acids. Chem. Soc. 1959, VI, 3485.

Wang, Y.; Lane, N. a.; Sun, C. N.; Fan, F.; Zawodzinski, T. A.; Sokolov, A. P. Ionic Conductivity and Glass Transition of Phosphoric Acids. J. Phys. Chem. B 2013, 117, 8003.

Baranov, A. I.; Shuvalov, L. A.; Shchagina, N. M. Superion conductivity and phase transitions in CsHSO4 and CsHSeo4 crystals. JETP Lett. 1982, 36 (11), 459.

Chisholm, C. R. I.; Haile, S. M. Superprotonic behavior of Cs2 (HSO4)(H2PO4)—a new solid acid in the CsHSO4—CsH2PO4 system. Solid State Ionics 2000, 136, 229.

Hayes, M. J.; Pepper, D. C. The Solubility of H2SO4 in 1, 2-Dichlorethane. Trans. Faraday Soc. 1961, 57, 432.

Davidowski, S. K.; Thompson, F.; Huang, W.; Hasani, M.; Amin, S. A.; Angell, C. A.; Yarger, J. L. NMR Characterization of Ionicity and Transport Properties for a Series of Diethylmethylamine Based Protic Ionic Liquids. J. Phys. Chem. B 2016, 120 (18), 4279.

Authorized Officer Kihwan Moon, International Preliminary Report on Patentability for PCT/US2014/029294, dated Sep. 24, 2015, 10 pages.

Authorized Officer Blaine R. Copenheaver, International Search Report and Written Opinion for PCT/US2014/029294, dated Jul. 29, 2014, 18 pages.

Cooper et al. (1986). "Ambient Temperature Plastic Crystal Fast Ion Conductors," Solid State Ionics 18 & 19, 570-576.

MacFarlane et al. (Dec. 1999). "Lithium-doped plastic crystal electrolytes exhibiting fast ion conduction for secondary batteries," Nature 402, 792-794.

Alarco et al. (2004). "The plastic-crystalline phase of succinonitrile as a universal matrix for solid-state ionic conductors," Nature Materials 3, 476-481.

Hayashi et al. (May 2012). "Superionic glass-ceramic electrolytes for room-temperature rechargeable sodium batteries," Nature Communications 3, 856.

Nishijima et al. (Jan. 2009). "Cathode properties of metal trifluorides in Li and Na secondary batteries," J. Power Sources 190, 558-562.

Park et al. (2007). "Discharge properties of all-solid sodium-sulfur battery using poly (ethylene oxide) electrolyte," J. Power Sources 165, 450-454.

Lu et al. (2010). "Advanced materials for sodium-beta alumina batteries: Status, challenges and perspectives," J. Power Sources 195, 2431-2442.

Mizuno et al. (Apr. 2005). "New, highly ion-conductive crystals precipitated from Li2S-P2S5 Glasses," Adv. Mater. 17, No. 7, 918-921.

Sakuda et al. (2010). "Interfacial Observation between LiCoO2 Electrode and Li2S-P2S5 Solid Electrolytes of All- Solid-State Lithium Secondary Batteries Using Transmission Electron Microscopy," Chem. Mater. 22, 949-956.

Long et al. (2003). "Fast ion conduction in olecular plastic crystals," Solid State Ionics 161, 105-112.

Derollez et al. (1990). "Structure of succinonitrile in its plastic phase," J. Phys. Condens. Matter 2, 6893-6903.

Volel et al. (2004). "Morphology and Nanomechanics of Conducting Plastic Crystals," Chem. Phys. Chem. 5, 1027-1033.

Nan et al. (Dec. 2003). "Enhanced Ionic Conductivity of Polymer Electrolytes Containing Nanocomposite SiO2 Particles," Phys. Rev. Lett. 91, No. 26, 104-108.

Bhattacharyya et al. (2004). "Second Phase Effects on the conductivity of Non-Aqueous Salt Solutions: "Soggy Sand Electrolytes"," Adv. Mater. 16, Nos. 9-10, 811-814.

Itoh et al. (2003). "Composite polymer electrolytes of poly(ethylene oxide)/BaTiO3/Li salt with hyperbranched polymer," J. Power Sources 119-121, 403-408.

Rey et al. (1998). "Infrared and Raman study of the PEO-LiTFSI polymer electrolyte," Electrochim. 43, Nos. 10-1, 1505-1510.

Gorecki et al. (2002). "NMR and Conductivity Study of Polymer Electrolytes in the Imide Family: P(EO)/Li[N (SO2CnF2n 1)(SO2CmF2m 1)]," Chem. Phys. Chem. 3, No. 7, 620-625.

Saboungi et al. (2000). "Sturucture of Liquid PEO-LiTFSI Electrolyte," Phys. Rev. Lett. 84, No. 24, 5536-5539.

Linert et al. (2002). "Anions of low Lewis basicity for ionic solid state electrolytes," Coord. Chem. Rev. 226, 137-141.

Tarascon et al. (1994). "New electrolyte compositions stable over the 0 to 5 V voltage range and compatible with the Lil +xMn204/ carbon Li-ion cells," Solid State Ionics 69, 293-305.

Lee et al. (2012) "Lithium salt solutions in mixed sulfone and sulfone-carbonate solvents, and a Walden plot analysis of the maximally conductive solutions," J. Phys. Chem. 116, 23915-23920.

Seki et al. (2006) "Lithium Secondary Batteries Using Modified-Imidazolium Room-Temperature Ionic Liquid," J. Phys. Chem. B 110, 10228-10230.

Sakaebe et al. (2003) "N-Methyl-N-propylpiperidinium bis(trifluoromethanesulfonyl)imide (PP13—TFSI)—novel electrolyte base for Li battery," Electrochem. Commun. 5, 594-598.

Cooper et al. (1983) "Versatile Organic Iodide Melts and Glasses with High Mole Fractions of LiI—Glass-Transition Temperatures and Electrical Conductivities," Solid State Ionics 9-10, 617-622.

Briant et al. (1980) "Ionic conductivity in Na+, K+, and Ag+ α"-alumina," J. Solid State Chem. 33, 385-390.

Kamaya et al. (Jul. 2011) "A lithium superionic conductor," Nature Materials 10, 682-686.

Hayashi et al. (2004) "Characterization of Li2S-P2S5 glass-ceramics as a solid electrolyte for lithium secondary batteries," Solid State Ionics 175, 683-686.

Hayashi et al. (2010) "Development of sulfide glass-ceramic electrolytes for all-solid-state lithium rechargeable batteries," J. Solid State Electrochem. 14, 1761-1767.

Bauer et al. (2010) "Relaxation dynamics and ionic conductivity in a fragile plastic crystal," J. Chem. Phys. 135, 144509.

Kim et al. (Jul. 2006) "Anomalous Ionic Conductivity Increase in Li2S+GeS2+GeO2 Glasses," J. Phys. Chem. 110, 16318-16325.

I. S. Klein et al. Silicon hydrogensulfates: solid acids with exceptional 25° C. conductivities and possible electrochemical device applications. J. Mater. Chem. A, 2017, 5, 14092-14100.

* cited by examiner

… (1)

ALKALI ION CONDUCTING PLASTIC CRYSTALS

CROSS-REFERENCE TO RELATED APPLICATIONS

This application claims the benefit of U.S. Application Ser. No. 62/526,963 filed on Jun. 29, 2017, and is a continuation-in-part of U.S. patent application Ser. No. 14/775,215 filed on Sep. 11, 2015, which is a U.S. National Phase Application of International Patent Application No. PCT/US2014/029294 filed Mar. 14, 2014, which claims the benefit of U.S. Application Ser. No. 61/782,292 filed on Mar. 14, 2013, the contents of all of which are incorporated herein by reference in their entirety.

STATEMENT OF GOVERNMENT INTEREST

This invention was made with government support under W911NF-11-1-0263 awarded by the Army Research Office. The government has certain rights in the invention.

TECHNICAL FIELD

This invention relates to alkali ion conducting plastic crystals suitable for solid state electrolytes in lithium ion batteries.

BACKGROUND

FIG. 1 depicts electrochemical device 100 having anode 102 and cathode 104. Anode 102 and cathode 104 are separated by separator 106. In one example, electrochemical device 100 is a lithium-ion battery (LIB). Anode 102 includes anode collector 108 and anode material 110 in contact with the anode collector. Cathode 104 includes cathode collector 112 and cathode material 114 in contact with the cathode collector. Electrolyte 116 is in contact with anode material 110 and cathode material 114. Anode collector 108 and cathode collector 112 are electrically coupled via closed external circuit 118. Anode material 110 and cathode material 114 are materials into which, and from which, alkali ions 120 can migrate. During insertion (or intercalation) alkali ions move into the electrode (anode or cathode) material. During extraction (or deintercalation), the reverse process, alkali ions move out of the electrode (anode or cathode) material. When an electrochemical device is discharging, alkali ions are extracted from the anode material and inserted into the cathode material. When the cell is charging, alkali ions are extracted from the cathode material and inserted into the anode material. The arrows in FIG. 1 depict movement of alkali ions through separator 106 during charging and discharging. FIG. 2 depicts electrochemical device 100 positioned in and configured to provide power to apparatus 200. Apparatus 200 may be, for example, a motorized vehicle.

A variety of electrolytes 116 have been used for moving alkali cations from anode to cathode compartments of electrochemical devices. In one example, Li$^+$ ions in a LIB are transported through a molecular solvent blend. The blend is used because no single solvent has been found to dissolve the preferred salt LiPF$_6$ and at the same time yield a sufficiently high ion mobility. Ion mobility can be increased by mixing a high polarity but viscous component with an equal amount of a low dielectric constant, low viscosity, co-solvent. A common electrolyte used in LIBs is LiPF$_6$ dissolved in 1:1 ethylene carbonate-dimethyl carbonate. In some cases, the solution is supported within a gel structure. This electrolyte sacrifices safety (flammability), iconicity, and transport number, but provides acceptable conductivity, and is suitable for use with high voltage cathodes.

A modification of the liquid electrolyte approach that eliminates the molecular solvent, with increase in safety, is the use of ionic liquid solvents for the lithium salt, but this strategy also has the problem that the lithium ion typically becomes the least mobile species in the mixture. This is due to its greater charge intensity that leads it to dominate the electrostatic (or charge polarization) competition for nearest neighbor anions so that it "digs itself a trap". This problem can typically be mitigated by choosing the least polarizable anions possible, hence the predominance of fluorinated anion species in electrolytes of this type. While cells with such electrolytes can function with high cyclability, the current, hence power, is restricted.

An alternative strategy for avoiding liquid and molecular solvents involves the use of organic cation salts in plastic crystalline states as solvents in which smaller amounts of lithium salts, usually with the same anions, can be dissolved. These electrolytes, however, demonstrate low conductivity and Li$^+$-trapping. Other electrolytes that have been explored include crystalline fast ion conductors like sodium β" alumina, LiSicon, and thiophosphogermanates, in which the alkali cation is generally the only mobile ion. These electrolytes, however, can have limited appeal based on factors such as toxicity. Moreover, with a few exceptions, their conductivities are typically below $10^{-2}$ S/cm at ambient temperature. Fast ion glassy and glass-ceramic electrolytes have also been investigated, but are limited by conductivities that rarely exceed $10^{-3}$ S/cm.

SUMMARY

A first general aspect includes a solid electrolyte represented by general formula Li$_y$SiR$_x$(MO$_4$), wherein:
x is an integer from 1 to 3 inclusive,
y=4−x,
each R present is independently C1-C3 alkyl or C1-C3 alkoxy, and
M is sulfur, selenium, or tellurium.

Implementations of the first general aspect may include one or more of the following features.

In some cases, each R present is independently C1-C3 alkyl. In certain cases, at least one R is methyl, at least one R is ethyl, or at least one R is propyl. In some cases, each R present is independently C1-C3 alkoxy. In certain cases, at least one R is methoxy, at least one R is ethoxy, or at least one R is propoxy. In some cases each R present is independently C1-C3 alkyl or independently C1-C3 alkoxy. M is typically sulfur, selenium, or tellurium. x is typically 1, 2, or 3.

In a second general aspect, a cell separator for an electrochemical device defines pores containing the solid electrolyte of the first general aspect.

In a third general aspect, a composition includes a mixture of two or more different solid electrolytes of the first general aspect.

In a fourth general aspect, making a solid electrolyte includes combining a phenylsilane and a first acid to yield a mixture including benzene and a second acid. The phenylsilane includes at least one C1-C3 alkyl substituent or at least one C1-C3 alkoxy substituent, and the first acid is typically a diprotic acid. The diprotic acid typically includes at least one of sulfuric acid, selenic acid, and telluric acid. At least one of an alkali halide, an alkali amide, or an alkali alkoxide is combined with the second acid to yield a product including the solid electrolyte of the first general aspect. The second acid can be in the form of a solid or a liquid. The product is typically in the form of a waxy solid.

Implementations of the third general aspect may include one or more of the following features.

The phenylsilane may be selected from the group consisting of trimethylphenylsilane, trimethoxyphenylsilane, methyldiethylphenylsilane, dimethylethylphenylsilane, diphenyldimethylsilane, dimethyldiphenylsilane, monomethyltriphenylsilane, triethylphenylsilane, methyldimethoxyphenylsilane, dimethylmethoxyphenylsilane, dimethylethoxyphenylsilane, methyldiethoxyphenylsilane, methylmethoxyethoxyphenylsilane, ethylmethoxyethoxyphenylsilane, triethoxyphenylsilane, methylethylpropylphenylsilane, methyldipropylphenylsilane, ethyldipropylphenylsilane, methypropyldiphenylsilane, methylpropyldiphenylsilane, ethylpropyldiphenylsilane, methylethylpropoxyphenylsilane, methyldipropoxyphenylsilane, dipropoxydiphenylsilane, methylethoxypropoxyphenylsilane, and ethoxypropoxydiphenylsilane. The alkali amide may be selected from the group consisting of lithium amides, sodium amides, and potassium amides. The alkali alkoxide may be selected from the group consisting of lithium alkoxides, sodium alkoxides, and potassium alkoxides. The alkali halide may be selected from the group consisting of lithium halides, sodium halides, and potassium halides. In some cases, the alkali halide is lithium chloride, sodium chloride, or potassium chloride.

Combining the phenylsilane and the first acid replaces a phenyl group of the phenylsilane with a hydrogen oxyacid group to yield a silane, where the oxyacid group typically includes sulfate, selenite, or tellurite.

In some implementations, the solid electrolyte is a first solid electrolyte, and the first solid electrolyte and a second solid electrolyte are combined to yield a composite solid electrolyte.

These general and specific aspects may be implemented using a device, system or method, or any combination of devices, systems, or methods. The details of one or more embodiments are set forth in the accompanying drawings and the description below. Other features, objects, and advantages will be apparent from the description and drawings, and from the claims.

DETAILED DESCRIPTION

Figure 1:
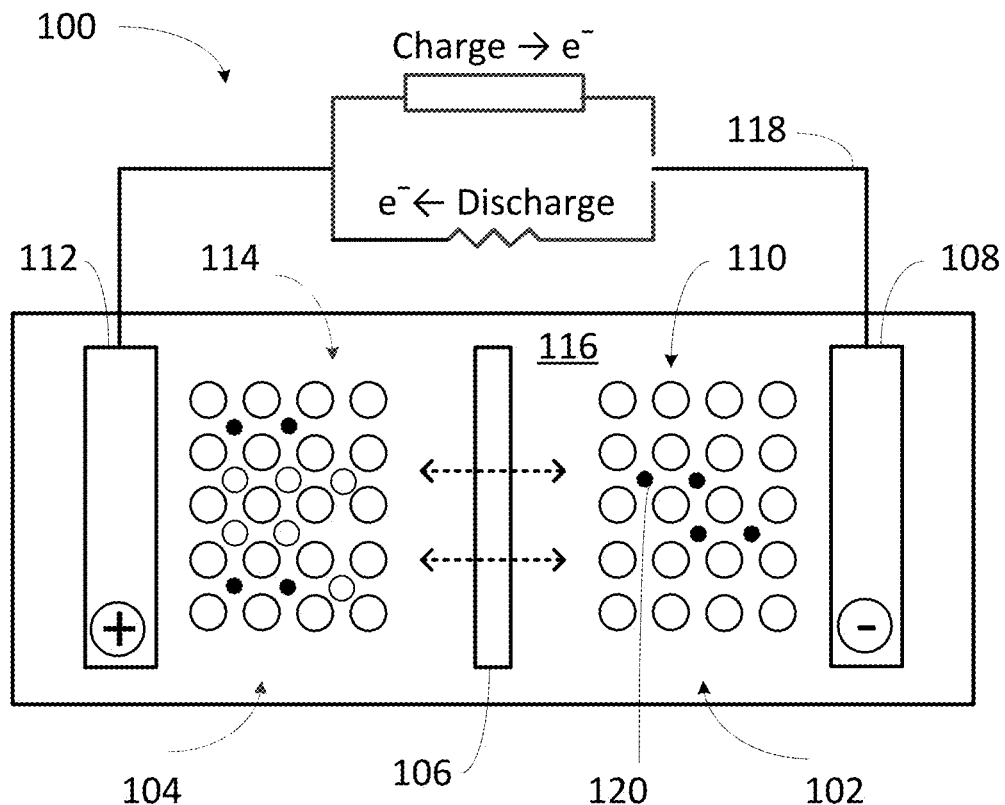
FIG. 1 depicts an electrochemical device.
Figure 2:
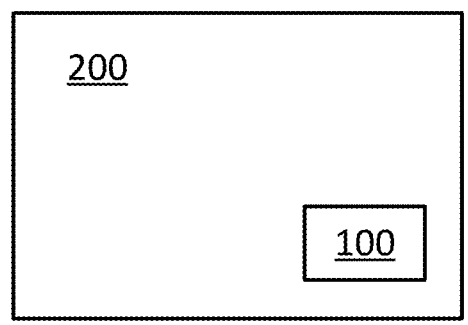
FIG. 2 depicts an apparatus including an electrochemical device.

Alkali ion conducting plastic crystal electrolytes (also referred to herein as plastic crystals, plastic crystal conductors, or single ion conductors) and synthesis thereof, are described herein. "Plastic crystal" generally refers to a mechanically soft crystal composed of weakly interacting molecules that possess some orientational or conformational internal degree of freedom. If the internal degree of freedom is molecular rotation, the plastic crystal may be referred to as a rotator phase crystal. Plastic crystals are typically characterized by the presence of asymmetric particles of globular or short tube-like character. They resemble waxes and are easily deformed. Plastic crystals may exhibit a glass transition (e.g., if they do not first reorganize to closer-packed non-rotator states). In contrast to glasses, however, which retain their shape only up to the glass transition temperature, where the shear modulus decays to zero on the 100 second time scale, plastic crystals retain their solidity (finite shear modulus) up to higher temperatures, limited by their melting points.

For plastic crystal conductors that contain loosely bound alkali ions, a class of solid electrolytes generally referred to herein as "ionic rotator phase conductors," the ability to remain solid above the glass transition temperature allows higher solid state ionic conductivities than those attained with glasses that have loosely bound alkali ions. These ionic rotator phase conductors include organic and solid electrolytes derived, for example, by replacing one or more of the atoms or groups B, in compounds having a formula $AB_x$, where A is a tetravalent to hexavalent atom (e.g., atoms from groups 4 and 14 to 16 of the periodic table, including Si, P, C, Ge, Ti, Zr, As, Te, and the like) and B is one or more different monovalent substituents including halogen atoms, C1-C3 alkyl groups, C1-C3 alkoxy groups, cyano groups, acetate groups, and the like, with a "hard" anion C (i.e., an anion that, in the sense of Pearson's "hard and soft acids and bases" (HSAB), provides an unpolarizable electron exterior), and then compensating the charge imbalance with an alkali cation. Hard anions C include, for example, oxyanions such as sulfate, selenite, fluorophosphate, trifluoromethane phosphate, and the like. As defined herein, a solid is a substance having a finite shear modulus which does not deform under its own weight at ambient temperatures. Solid as defined here may include malleable solids and compositions having deformable or moldable properties. According to this definition, waxes are one example of a solid material.

The charge compensating alkali cation(s), being monovalent, is weakly bound and moves freely through the plastic crystal phase produced by facile rotation of the anion. Rotationally disordered solids are referred to herein as ionic rotator phase conductors and represented as the neutral species $[AB_{x-y}C_y]^{y-}[M]_y^+$, in which A is a tetravalent to hexavalent atom; B is a monovalent ligand; C is a hard anion; and M is an alkali metal; x is 4 when A is tetravalent, x is 5 when A is pentavalent, and x is 6 when A is hexavalent; and y is an integer from 1 to x−1 inclusive. The ionic conductivity of these ionic phase rotator conductors is high, making these solid state alkali conducting materials suitable for use in lithium ion batteries and other electrochemical devices.

In one example, a plastic crystal based on $SiCl_4$ is formed as an anion with silicon at the center and charge compensated by an alkali cation that moves freely through the plastic crystal phase produced by the facile rotation of the anion. To convert the $SiCl_4$ molecule to an anion without destroying a facile axis of rotation, one or more of the chlorine atoms is replaced by a hard anion carrying a higher charge than chlorine and occupying a comparable volume, and the charge imbalance is compensated with an alkali cation. This ionic phase rotator conductor is represented by the general formula $[SiCl_{(4-y)}(SO_4)_y]^{y-}[M]^+_y$, where y is an integer from 1 to 3 inclusive and M is an alkali atom (e.g., $[SiCl_3SO_4]^-[Li]^+$ when y=1). Other examples include derivatives of compounds $AB_x$ where A is carbon (e.g., $CCl_4$, $C(OEt)_4$, $C(OAc)_4$, etc.), P ($PCl_5$, $P(OEt)_4$), and the like, to yield ionic phase rotator conductors such as $[PCl_{(5-y)}SO_4)_y]^{y-}[M]_y^+$, where y is an integer in a range from 1 to 4 inclusive and M is an alkali ion, and $[CCl_{(4-y)}SO_4)_y]^{y-}[M]_y^+$, where y is an integer in a range from 1 to 3 inclusive, and M is an alkali atom. In other cases, reactants will vary based on the identity of A, B, C, and M in the chemical formula $[AB_{x-y}C_y]^{y-}[M]_y^+$.

Figure 3:
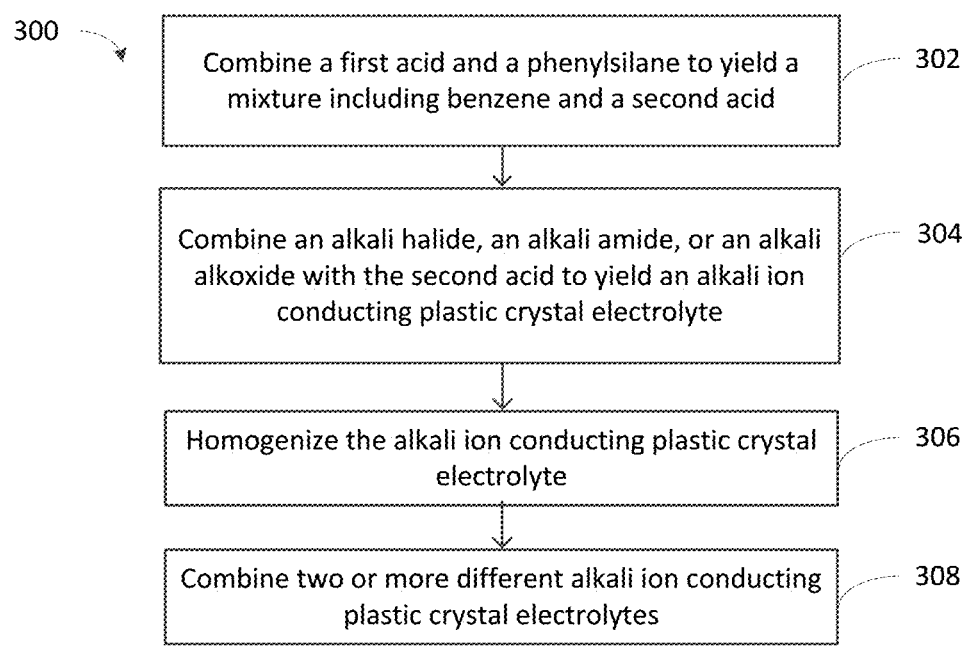
FIG. 3 is a flow chart showing synthesis of an alkali ion conducting plastic crystal electrolyte.

FIG. 3 is a flow chart showing process 300 for preparation of plastic crystal electrolytes from phenylsilanes. In 302, a diprotic acid and a phenylsilane are combined to yield a mixture including benzene and a second acid. Examples of suitable diprotic acids include anhydrous sulfuric acid, selenic acid, and telluric acid. The second acid may be in the form of a liquid or in the form of a solid at ambient temperature and pressure. The benzene is then separated (e.g., decanted) from the second acid. In 304, at least one of an alkali halide, an alkali amide, or an alkali alkoxide is combined with the second acid formed in 302 to yield a plastic crystal electrolyte. The plastic crystal electrolyte is typically in the form of a soft, waxy product. The alkali halide is typically a lithium halide, a sodium halide, or a potassium halide. In one example, the halide is a chloride. The alkali amide is typically a lithium amide, a sodium amide, or a potassium amide. The alkali alkoxide is typically a lithium alkoxide, a sodium alkoxide, or a potassium alkoxide. The plastic crystal electrolyte may be homogenized in 306 (e.g., in a ball mill, mortar and pestle, or similar apparatus known in the art). In 308, two or more different alkali ion plastic crystal electrolytes are combined to yield a composite solid electrolyte, thereby stabilizing the solid electrolyte to inhibit or prevent recrystallization to the ordered plastic crystal phase. In some cases, a composite solid electrolyte is prepared by combining a mixture of two or more different phenylsilanes in 302. One example of a mixture of two or more different phenylsilanes includes a mixture of trimethylphenylsilane and dimethylphenylsilane. Step 308 may not be implemented in all instances.

For the plastic crystal electrolytes or ionic rotator phase conductors $[AB_{z-x}C_x]^{x-}[M]_x^-$ described herein, M is the mobile species and A is a high charge (oxidation number) Lewis acid species. That is, electrolytes that contain elements in their maximum oxidation states (oxygen excepted), are typically inert to oxidizing conditions at cathodes.

Alkali Ion Conducting Plastic Crystals

The reaction of $SiCl_4$ with $H_2SO_4$ yields the fully hydrogensulfated compound $Si(SO_4H)_4$, a plastic crystal with a high proton conductivity. On $LiNH_2$ neutralization, it yields a soft solid lithium salt $Li_4Si(SO_4)_4$, that also has a high conductivity.

Alkali ion conductors described herein are produced as soft deformable solids by the solid state neutralization of mono hydrogensulfate solid acids of $-SiX_3$, using anhydrous lithium amide, according to Equation (1):

$$SiX_3SO_4H(s) + LiNH_2(s) \rightarrow SiX_3SO_4Li(s) + NH_3(g) \qquad (1)$$

where the silicon ligands (X) can be as many as there are polyphenylated silane precursors $(Si(Ph)_nX_{(4-n)})$ available for selective reaction with sulfuric acid. When n=1, a monoprotic acid is obtained due to the favorable leaving kinetics of the phenyl group in the acid according to Equation (2):

$$Si(Ph)_nX_{(4-n)} + H_2SO_4 \rightarrow SiX_{(4-n)}(SO_4H)_n + nC_6H_6 \qquad (2)$$

The 4−n silicon ligands need not all be the same if precursors with mixed alkyl and alkoxy groups are used in combination with the phenyl ligand. Suitable examples of silicon ligands include trimethoxy-, triethoxy-, and trimethylphenylsilanes, which yield singly lithiated lithium salts of trimethoxy-, triethoxy-, and trimethyl silyl hydrogen sulfate, respectively. One advantage of using phenylated precursors is that the phenyl ligand can be more easily displaced by protonation than other ligands, such that a pure product can be obtained, for example, by decantation of the product benzene, followed by drying. In this manner, the phenyl group may be replaced by a hydrogen oxyacid group. The oxyacid group may include sulfate, selenite, or tellurite, and the silicon ligands may independently include one or more C1-C3 alkyl substituents, one or more C1-C3 alkoxy substituents, or a combination thereof. In the case of the trimethyl compound, the product was confirmed by the presence of a single sharp $^{29}Si$ resonance in the precursor acid phase, which was a liquid. In the other cases, some residual phenyl groups were implied by the presence of two $^{29}$Si resonances in the precursor acid spectra.

Alkali ion conducting, non-doped plastic crystals having lithium ions as an integral part of the structure are described. These plastic crystals are salts of alkali cations in which the alkali cations take advantage of rotation of large anions to move freely through the waxy solid medium (glass-like transition at −85° C.), with particular advantages at sub-zero temperatures. The alkali cation is mobile, while other species are substantially immobile. The second nearest neighbor of the alkali cation is a high charge (oxidation number) Lewis acid species, in the present cases, S(VI). The plastic crystals contain anions in which silicon is ligated with sulfate and one or more other ligands (e.g., one or more of halides, alkyl groups, and alkoxy groups). In certain cases, one or more of the ligands may be involatile, non-flammable or weakly flammable, and inoxidizable. Near −90° C., the plastic crystals exhibit a glass-like transition where the rotational relaxation time exceeds the measuring time scale. The plastic crystals have conductivities of 3 to 10 mS/cm at room temperature and are suitable for use as solid state electrolytes. In one example, the electrolytes maintain a highly conductive state at temperatures as low as −30° C.

Plastic crystals can be advantageous over glasses. Glasses only retain their shape up to the glass transition temperature, $T_g$, where the shear modulus decays to zero on the 100 sec time scale. Plastic crystals usually exhibit a glass transition, but in contrast to glasses, they retain their solidity (finite shear modulus) up to higher temperatures. Thus, higher solid state conductivities may be achieved with plastic crystals than can be attained with superionic glasses.

Plastic crystals including complexes represented by the general formula $Li_ySiR_x(MO_4)_y$, where x is an integer from 1 to 3 inclusive, y=4−x, each R present is independently C1-C3 alkyl, C1-C3 alkoxy, and M is sulfur, selenium, or tellurium. Examples are provided in Tables 1-6.

TABLE 1

Examples of plastic crystals, $Li_ySiR_x(MO_4)_y$ with M = S

| Plastic Crystal | x | y | R |
| --- | --- | --- | --- |
| $Li_3SiCH_3(SO_4)_3$ | 1 | 3 | —$CH_3$ |
| $Li_2Si(CH_3)_2(SO_4)_2$ | 2 | 2 | —$CH_3$ |
| $LiSi(CH_3)_3(SO_4)$ | 3 | 1 | —$CH_3$ |
| $Li_3Si(CH_2CH_3)(SO_4)_3$ | 1 | 3 | —$CH_2CH_3$ |
| $Li_2Si(CH_2CH_3)_2(SO_4)_2$ | 2 | 2 | —$CH_2CH_3$ |
| $LiSi(CH_2CH_3)_3(SO_4)$ | 3 | 1 | —$CH_2CH_3$ |
| $Li_3Si(CH_2CH_2CH_3)(SO_4)_3$ | 1 | 3 | —$(CH_2)_2CH_3$ |
| $Li_2Si(CH_2CH_2CH_3)_2(SO_4)_2$ | 2 | 2 | —$(CH_2)_2CH_3$ |
| $LiSi(CH_2CH_2CH_3)_3(SO_4)$ | 3 | 1 | —$(CH_2)_2CH_3$ |
| $Li_2Si(CH_3)(CH_2CH_3)(SO_4)_2$ | 2 | 2 | —$CH_3$, —$CH_2CH_3$ |
| $Li_2Si(CH_3)(CH_2CH_2CH_3)(SO_4)_2$ | 2 | 2 | —$CH_3$, —$(CH_2)_2CH_3$ |
| $Li_2Si(CH_2CH_3)(CH_2CH_2CH_3)(SO_4)_2$ | 2 | 2 | —$CH_2CH_3$, —$(CH_2)_2CH_3$ |
| $LiSi(CH_3)_2(CH_2CH_3)(SO_4)$ | 1 | 3 | —$CH_3$, —$CH_3$, —$CH_2CH_3$ |
| $LiSi(CH_3)(CH_2CH_3)_2(SO_4)$ | 1 | 3 | —$CH_3$,—$CH_2CH_3$, —$CH_2CH_3$ |
| $LiSi(CH_3)(CH_2CH_3)(CH_2CH_2CH_3)(SO_4)$ | 1 | 3 | —$CH_3$, —$CH_2CH_3$, —$(CH_2)_2CH_3$ |
| $LiSi(CH_3)(CH_2CH_2CH_3)_2(SO_4)$ | 1 | 3 | —$CH_3$, —$(CH_2)_2CH_3$, —$(CH_2)_2CH_3$ |
| $LiSi(CH_2CH_3)(CH_2CH_3)(CH_2CH_2CH_3)(SO_4)$ | 1 | 3 | —$CH_2CH_3$, —$CH_2CH_3$, —$(CH_2)_2CH_3$ |
| $LiSi(CH_2CH_3)(CH_2CH_2CH_3)_2(SO_4)$ | 1 | 3 | —$CH_2CH_3$, —$(CH_2)_2CH_3$, —$(CH_2)_2CH_3$ |

TABLE 2

Examples of plastic crystals, $Li_ySiR_x(MO_4)_y$ with M = S

| Plastic Crystal | x | y | R |
| --- | --- | --- | --- |
| $Li_3SiOCH_3(SO_4)_3$ | 1 | 3 | —$OCH_3$ |
| $Li_2Si(OCH_3)_2(SO_4)_2$ | 2 | 2 | —$OCH_3$ |
| $LiSi(OCH_3)_3(SO_4)$ | 3 | 1 | —$OCH_3$ |
| $Li_3Si(OCH_2CH_3)(SO_4)_3$ | 1 | 3 | —$OCH_2CH_3$ |
| $Li_2Si(OCH_2CH_3)_2(SO_4)_2$ | 2 | 2 | —$OCH_2CH_3$ |
| $LiSi(OCH_2CH_3)_3(SO_4)$ | 3 | 1 | —$OCH_2CH_3$ |
| $Li_3Si(OCH_2CH_2CH_3)(SO_4)_3$ | 1 | 3 | —$O(CH_2)_2CH_3$ |
| $Li_2Si(OCH_2CH_2CH_3)_2(SO_4)_2$ | 2 | 2 | —$O(CH_2)_2CH_3$ |
| $LiSi(OCH_2CH_2CH_3)_3(SO_4)$ | 3 | 1 | —$O(CH_2)_2CH_3$ |
| $Li_2Si(OCH_3)(OCH_2CH_3)(SO_4)_2$ | 2 | 2 | —$OCH_3$, —$OCH_2CH_3$ |
| $Li_2Si(OCH_3)(OCH_2CH_2CH_3)(SO_4)_2$ | 2 | 2 | —$OCH_3$, —$O(CH_2)_2CH_3$ |
| $Li_2Si(OCH_2CH_3)(OCH_2CH_2CH_3)(SO_4)_2$ | 2 | 2 | —$OCH_2CH_3$, —$O(CH_2)_2CH_3$ |
| $LiSi(OCH_3)_2(OCH_2CH_3)(SO_4)$ | 1 | 3 | —$OCH_3$, —$OCH_3$, —$OCH_2CH_3$ |
| $LiSi(OCH_3)(OCH_2CH_3)_2(SO_4)$ | 1 | 3 | —$OCH_3$, —$OCH_2CH_3$, —$OCH_2CH_3$ |
| $LiSi(OCH_3)(OCH_2CH_3)(OCH_2CH_2CH_3)(SO_4)$ | 1 | 3 | —$OCH_3$, —$OCH_2CH_3$, —$O(CH_2)_2CH_3$ |
| $LiSi(OCH_3)(OCH_2CH_2CH_3)_2(SO_4)$ | 1 | 3 | —$OCH_3$, —$O(CH_2)_2CH_3$, —$O(CH_2)_2CH_3$ |
| $LiSi(OCH_2CH_3)(OCH_2CH_3)(OCH_2CH_2CH_3)(SO_4)$ | 1 | 3 | —$OCH_2CH_3$, —$OCH_2CH_3$, —$O(CH_2)_2CH_3$ |
| $LiSi(OCH_2CH_3)(OCH_2CH_2CH_3)_2(SO_4)$ | 1 | 3 | —$OCH_2CH_3$, —$O(CH_2)_2CH_3$, —$O(CH_2)_2CH_3$ |

TABLE 3

Examples of plastic crystals, $Li_ySiR_x(MO_4)_y$, with M = Se

| Plastic Crystal | x | y | R |
|---|---|---|---|
| $Li_3SiCH_3(SeO_4)_3$ | 1 | 3 | $-CH_3$ |
| $Li_2Si(CH_3)_2(SeO_4)_2$ | 2 | 2 | $-CH_3$ |
| $LiSi(CH_3)_3(SeO_4)$ | 3 | 1 | $-CH_3$ |
| $Li_3Si(CH_2CH_3)(SeO_4)_3$ | 1 | 3 | $-CH_2CH_3$ |
| $Li_2Si(CH_2CH_3)_2(SeO_4)_2$ | 2 | 2 | $-CH_2CH_3$ |
| $LiSi(CH_2CH_3)_3(SeO_4)$ | 3 | 1 | $-CH_2CH_3$ |
| $Li_3Si(CH_2CH_2CH_3)(SeO_4)_3$ | 1 | 3 | $-(CH_2)_2CH_3$ |
| $Li_2Si(CH_2CH_2CH_3)_2(SeO_4)_2$ | 2 | 2 | $-(CH_2)_2CH_3$ |
| $LiSi(CH_2CH_2CH_3)_3(SeO_4)$ | 3 | 1 | $-(CH_2)_2CH_3$ |
| $Li_2Si(CH_3)(CH_2CH_3)(SeO_4)_2$ | 2 | 2 | $-CH_2, -CH_2CH_3$ |
| $Li_2Si(CH_3)(CH_2CH_2CH_3)(SeO_4)_2$ | 2 | 2 | $-CH_3, -(CH_2)_2CH_3$ |
| $Li_2Si(CH_2CH_3)(CH_2CH_2CH_3)(SeO_4)_2$ | 2 | 2 | $-CH_2CH_3, -(CH_2)_2CH_3$ |
| $LiSi(CH_3)_2(CH_2CH_3)(SeO_4)$ | 1 | 3 | $-CH_3, -CH_3, -CH_2CH_3$ |
| $LiSi(CH_3)(CH_2CH_3)_2(SeO_4)$ | 1 | 3 | $-CH_3, -CH_2CH_3, -CH_2CH_3$ |
| $LiSi(CH_3)(CH_2CH_3)(CH_2CH_2CH_3)(SeO_4)$ | 1 | 3 | $-CH_3, -CH_2CH_3, -(CH_2)_2CH_3$ |
| $LiSi(CH_3)(CH_2CH_2CH_3)_2(SeO_4)$ | 1 | 3 | $-CH_3, -(CH_2)_2CH_3, -(CH_2)_2CH_3$ |
| $LiSi(CH_2CH_3)(CH_2CH_3)(CH_2CH_2CH_3)(SeO_4)$ | 1 | 3 | $-CH_2CH_3, -CH_2CH_3, -(CH_2)_2CH_3$ |
| $LiSi(CH_2CH_3)(CH_2CH_2CH_3)_2(SeO_4)$ | 1 | 3 | $-CH_2CH_3, -(CH_2)_2CH_3, -(CH_2)_2CH_3$ |

TABLE 4

Examples of plastic crystals, $Li_ySiR_x(MO_4)_y$, with M = Se

| Plastic Crystal | x | y | R |
|---|---|---|---|
| $Li_3SiOCH_3(SeO_4)_3$ | 1 | 3 | $-OCH_3$ |
| $Li_2Si(OCH_3)_2(SeO_4)_2$ | 2 | 2 | $-OCH_3$ |
| $LiSi(OCH_3)_3(SeO_4)$ | 3 | 1 | $-OCH_3$ |
| $Li_3Si(OCH_2CH_3)(SeO_4)_3$ | 1 | 3 | $-OCH_2CH_3$ |
| $Li_2Si(OCH_2CH_3)_2(SeO_4)_2$ | 2 | 2 | $-OCH_2CH_3$ |
| $LiSi(OCH_2CH_3)_3(SeO_4)$ | 3 | 1 | $-OCH_2CH_3$ |
| $Li_3Si(OCH_2CH_2CH_3)(SeO_4)_3$ | 1 | 3 | $-O(CH_2)_2CH_3$ |
| $Li_2Si(OCH_2CH_2CH_3)_2(SeO_4)_2$ | 2 | 2 | $-O(CH_2)_2CH_3$ |
| $LiSi(OCH_2CH_2CH_3)_3(SeO_4)$ | 3 | 1 | $-O(CH_2)_2CH_3$ |
| $Li_2Si(OCH_3)(OCH_2CH_3)(SeO_4)_2$ | 2 | 2 | $-OCH_3, -OCH_2CH_3$ |
| $Li_2Si(OCH_3)(OCH_2CH_2CH_3)(SeO_4)_2$ | 2 | 2 | $-OCH_3, -O(CH_2)_2CH_3$ |
| $Li_2Si(OCH_2CH_3)(OCH_2CH_2CH_3)(SeO_4)_2$ | 2 | 2 | $-OCH_2CH_3, -O(CH_2)_2CH_3$ |
| $LiSi(OCH_3)_2(OCH_2CH_3)(SeO_4)$ | 1 | 3 | $-OCH_3, -OCH_3, -OCH_2CH_3$ |
| $LiSi(OCH_3)(OCH_2CH_3)_2(SeO_4)$ | 1 | 3 | $-OCH_3, -OCH_2CH_3, -OCH_2CH_3$ |
| $LiSi(OCH_3)(OCH_2CH_3)(OCH_2CH_2CH_3)(SeO_4)$ | 1 | 3 | $-OCH_3, -OCH_2CH_3, -O(CH_2)_2CH_3$ |
| $LiSi(OCH_3)(OCH_2CH_2CH_3)_2(SeO_4)$ | 1 | 3 | $-OCH_3, -O(CH_2)_2CH_3, -O(CH_2)_2CH_3$ |
| $LiSi(OCH_2CH_3)(OCH_2CH_3)(OCH_2CH_2CH_3)(SeO_4)$ | 1 | 3 | $-OCH_2CH_3, -OCH_2CH_3, -O(CH_2)_2CH_3$ |
| $LiSi(OCH_2CH_3)(OCH_2CH_2CH_3)_2(SeO_4)$ | 1 | 3 | $-OCH_2CH_3, -O(CH_2)_2CH_3, -O(CH_2)_2CH_3$ |

TABLE 5

Examples of plastic crystals, $Li_ySiR_x(MO_4)_y$, with M = Te

| Plastic Crystal | x | y | R |
|---|---|---|---|
| $Li_3SiCH_3(TeO_4)_3$ | 1 | 3 | $-CH_3$ |
| $Li_2Si(CH_3)_2(TeO_4)_2$ | 2 | 2 | $-CH_3$ |
| $LiSi(CH_3)_3(TeO_4)$ | 3 | 1 | $-CH_3$ |
| $Li_3Si(CH_2CH_3)(TeO_4)_3$ | 1 | 3 | $-CH_2CH_3$ |
| $Li_2Si(CH_2CH_3)_2(TeO_4)_2$ | 2 | 2 | $-CH_2CH_3$ |
| $LiSi(CH_2CH_3)_3(TeO_4)$ | 3 | 1 | $-CH_2CH_3$ |
| $Li_3Si(CH_2CH_2CH_3)(TeO_4)_3$ | 1 | 3 | $-(CH_2)_2CH_3$ |
| $Li_2Si(CH_2CH_2CH_3)_2(TeO_4)_2$ | 2 | 2 | $-(CH_2)_2CH_3$ |
| $LiSi(CH_2CH_2CH_3)_3(TeO_4)$ | 3 | 1 | $-(CH_2)_2CH_3$ |
| $Li_2Si(CH_3)(CH_2CH_3)(TeO_4)_2$ | 2 | 2 | $-CH_2, -CH_2CH_3$ |
| $Li_2Si(CH_3)(CH_2CH_2CH_3)(TeO_4)_2$ | 2 | 2 | $-CH_3, -(CH_2)_2CH_3$ |
| $Li_2Si(CH_2CH_3)(CH_2CH_2CH_3)(TeO_4)_2$ | 2 | 2 | $-CH_2CH_3, -(CH_2)_2CH_3$ |
| $LiSi(CH_3)_2(CH_2CH_3)(TeO_4)$ | 1 | 3 | $-CH_3, -CH_3, -CH_2CH_3$ |
| $LiSi(CH_3)(CH_2CH_3)_2(TeO_4)$ | 1 | 3 | $-CH_3, -CH_2CH_3, -CH_2CH_3$ |
| $LiSi(CH_3)(CH_2CH_3)(CH_2CH_2CH_3)(TeO_4)$ | 1 | 3 | $-CH_3, -CH_2CH_3, -(CH_2)_2CH_3$ |

TABLE 5-continued

Examples of plastic crystals, $Li_ySiR_x(MO_4)_y$, with M = Te

| Plastic Crystal | x | y | R |
|---|---|---|---|
| $LiSi(CH_3)(CH_2CH_2CH_3)_2(TeO_4)$ | 1 | 3 | $-CH_3, -(CH_2)_2CH_3, -(CH_2)_2CH_3$ |
| $LiSi(CH_2CH_3)(CH_2CH_3)(CH_2CH_2CH_3)(TeO_4)$ | 1 | 3 | $-CH_2CH_3, -CH_2CH_3, -(CH_2)_2CH_3$ |
| $LiSi(CH_2CH_3)(CH_2CH_2CH_3)_2(TeO_4)$ | 1 | 3 | $-CH_2CH_3, -(CH_2)_2CH_3, -(CH_2)_2CH_3$ |

TABLE 6

Examples of plastic crystals, $Li_ySiR_x(MO_4)_y$, with M = Te

| Plastic Crystal | x | y | R |
|---|---|---|---|
| $Li_3SiOCH_3(TeO_4)_3$ | 1 | 3 | $-OCH_3$ |
| $Li_2Si(OCH_3)_2(TeO_4)_2$ | 2 | 2 | $-OCH_3$ |
| $LiSi(OCH_3)_3(TeO_4)$ | 3 | 1 | $-OCH_3$ |
| $Li_3Si(OCH_2CH_3)(TeO_4)_3$ | 1 | 3 | $-OCH_2CH_3$ |
| $Li_2Si(OCH_2CH_3)_2(TeO_4)_2$ | 2 | 2 | $-OCH_2CH_3$ |
| $LiSi(OCH_2CH_3)_3(TeO_4)$ | 3 | 1 | $-OCH_2CH_3$ |
| $Li_3Si(OCH_2CH_2CH_3)(TeO_4)_3$ | 1 | 3 | $-O(CH_2)_2CH_3$ |
| $Li_2Si(OCH_2CH_2CH_3)_2(TeO_4)_2$ | 2 | 2 | $-O(CH_2)_2CH_3$ |
| $LiSi(OCH_2CH_2CH_3)_3(TeO_4)$ | 3 | 1 | $-O(CH_2)_2CH_3$ |
| $Li_2Si(OCH_3)(OCH_2CH_3)(TeO_4)_2$ | 2 | 2 | $-OCH_3, -OCH_2CH_3$ |
| $Li_2Si(OCH_3)(OCH_2CH_2CH_3)(TeO_4)_2$ | 2 | 2 | $-OCH_3, -O(CH_2)_2CH_3$ |
| $Li_2Si(OCH_2CH_3)(OCH_2CH_2CH_3)(TeO_4)_2$ | 2 | 2 | $-OCH_2CH_3, -O(CH_2)_2CH_3$ |
| $LiSi(OCH_3)_2(OCH_2CH_3)(TeO_4)$ | 1 | 3 | $-OCH_3, -OCH_3, -OCH_2CH_3$ |
| $LiSi(OCH_3)(OCH_2CH_3)_2(TeO_4)$ | 1 | 3 | $-OCH_3, -OCH_2CH_3, -OCH_2CH_3$ |
| $LiSi(OCH_3)(OCH_2CH_3)(OCH_2CH_2CH_3)(TeO_4)$ | 1 | 3 | $-OCH_3, -OCH_2CH_3, -O(CH_2)_2CH_3$ |
| $LiSi(OCH_3)(OCH_2CH_2CH_3)_2(TeO_4)$ | 1 | 3 | $-OCH_3, -O(CH_2)_2CH_3, -O(CH_2)_2CH_3$ |
| $LiSi(OCH_2CH_3)(OCH_2CH_3)(OCH_2CH_2CH_3)(TeO_4)$ | 1 | 3 | $-OCH_2CH_3, -OCH_2CH_3, -O(CH_2)_2CH_3$ |
| $LiSi(OCH_2CH_3)(OCH_2CH_2CH_3)_2(TeO_4)$ | 1 | 3 | $-OCH_2CH_3, -O(CH_2)_2CH_3, -O(CH_2)_2CH_3$ |

Other embodiments include plastic electrolytes in which x in $Li_ySiR_x(MO_4)_y$ is at least 2, and at least one R is C1-C3 alkyl and at least one R is C1-C3 alkoxy.

EXAMPLES

Preparation of Exemplary Plastic Crystal Electrolytes

Example 1: Li4

4 moles of nominally anhydrous sulfuric acid are added to 1 mol of silicon tetrachloride (with 50% excess in mass) under nitrogen atmosphere. The mixture was kept at room temperature and stirred for 5 hours to yield a colorless, transparent liquid and a small quantity of a white, gel-like solid (less than 1% in mass of total product). The solid was separated from the liquid by centrifugation for 2 hours. 4 moles of lithium amide (LiNH$_2$) were added to the liquid product, under nitrogen atmosphere and constant stirring. A slight excess of the amide (10% in moles) was subsequently added to ensure the completion of the reaction. The resulting white, waxy solid was homogenized in a ball mill for 1 hour to yield the plastic crystal electrolyte referred to herein as "Li4." Li4 exhibits an endothermic transition at 120° C. that may be an order-disorder (OD) transition for the rotation of the anions. A possible structure of Li4 is $Li_4Si(SO_4)_4$.

Example 2: Li2

2 moles of nominally anhydrous sulfuric acid were added to 1 mol of silicon tetrachloride (with 50% excess in mass) under nitrogen atmosphere. The mixture was kept at room temperature and stirred for 5 hours to yield a colorless, transparent liquid and a small quantity of a white, gel-like solid. The solid was separated from the liquid by centrifugation for 2 hours. 2 moles of lithium amide were then added to the liquid product, under nitrogen atmosphere and constant stirring. A slight excess of the amide (10% in moles) was subsequently added to ensure the completion of the reaction. The resulting white, waxy solid obtained was homogenized in a ball mill for 1 hour to yield the plastic crystal electrolyte referred to herein as "Li2." From calorimetric (differential scanning calorimetry) studies, Li2 is shown to have an initial "order-disorder" (OD) type of transition with peak at 80° C. Not to be bound by theory, it is believed that Li2 may have a chemical formula of $Li_2Si(SO_4)_2Cl_2$.

Example 3: Li3

3 moles of nominally anhydrous sulfuric acid were added to 1 mol of silicon tetrachloride (with 50% excess in mass) under nitrogen atmosphere. The mixture was kept at room temperature and stirred for 5 hours to yield a colorless, transparent liquid and a small quantity of a white, gel-like solid. The solid was separated from the liquid by centrifugation for 2 hours. 3 moles of lithium amide were then added to the liquid product, under nitrogen atmosphere and constant stirring. A slight excess of the amide (10% in moles) was subsequently added to ensure the completion of the reaction. The white, waxy solid obtained was homogenized in a ball mill for 1 hour to yield the plastic crystal electrolyte referred to herein as "Li3." Li3 has an initial OD temperature of 80° C. Not to be bound by theory, it is believed that Li3 may have a chemical formula of $Li_3Si(SO_4)_3Cl$.

Figure 4:
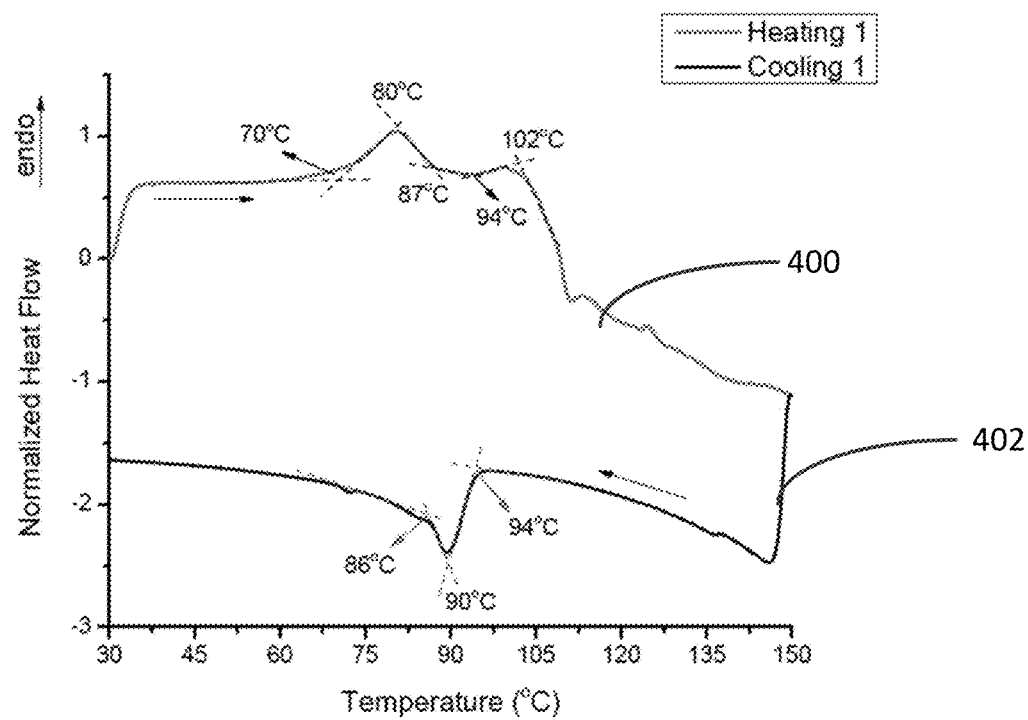
FIG. 4 shows a differential scanning calorimetry (DSC) scan for an alkali ion conducting plastic crystal electrolyte immediately after preparation.

FIG. 4 is a plot of the heat flow in a differential scanning calorimeter during increase of temperature on a sample of freshly prepared Li3 plastic crystal (plot 400), and then on subsequent cooling (plot 402), as indicated by arrows. The two peaks representing the end of the rotational disordering process during heating become a single lambda-like peak during cooling, and as seen more clearly in the scans made the next day shown in FIG. 5.

Figure 5:
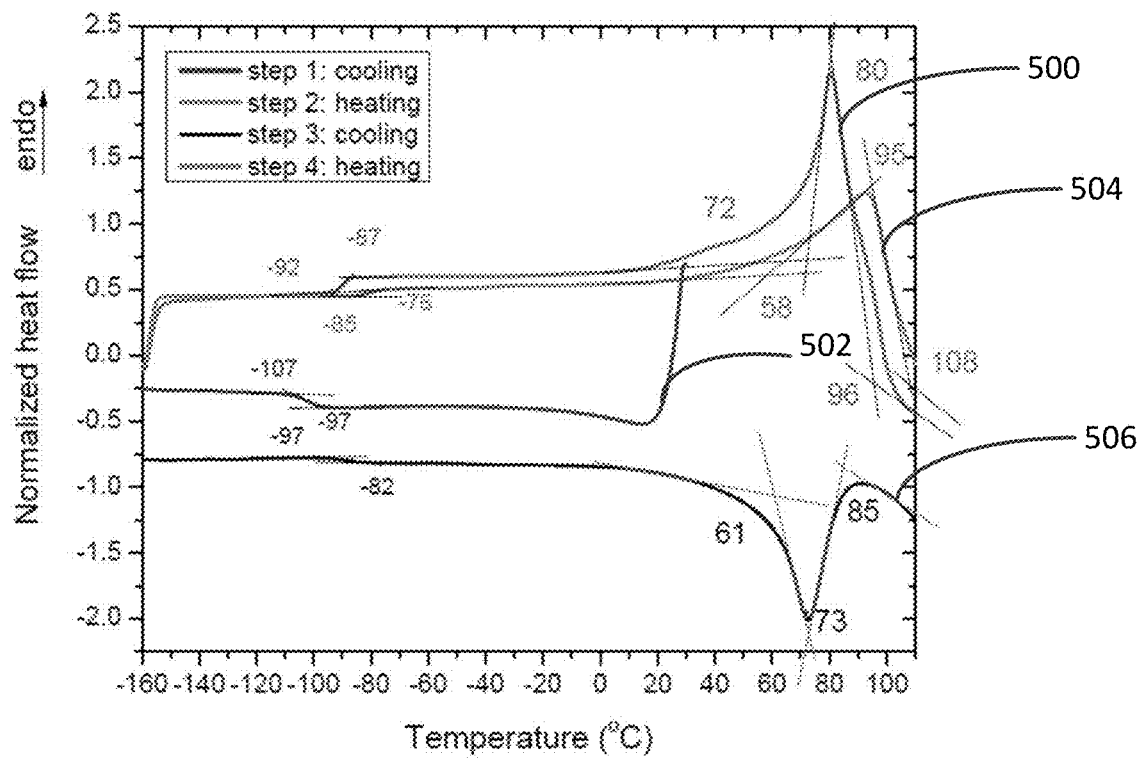
FIG. 5 shows full temperature range DSC scans for the alkali ion conducting plastic crystal electrolyte of FIG. 4.

FIG. 5 shows a sequence of DSC scans including plots 500, 502, 504, and 506 corresponding to the first heating, first cooling, second heating, and second cooling scans, respectively. The scans include the low temperature part of the thermal excitation process (i.e. the low temperature part of the FIG. 4 scans), showing that the lambda transition believed to mark the complete disordering of the anion rotations in the crystal, on heating terminates during cooling in the arrest of the ordering process at a glass transition. It is seen that the ordering process that (during cooling) begins abruptly at 85° C. (plot 506) ends in a (cooling) glass transition at –82° C. as the rotational degrees of freedom are arrested in a glass transition. This cooling glass transition is not as sharp as the one observed at –97° C. on the initial cooling (plot 502), which then became an onset heating glass transition at –92° C. on first complete heating (plot 500) for which the peak heat capacity was reached at 80° C. The state of the system is observed to be somewhat irreproducible once the heating has been taken above the transition temperature.

Except for the drift with time, FIG. 5 shows the characteristics of a cooperative disordering transition (commonly called a "lambda" transition) with a critical point, at which the order parameter falls to zero, at 80° C. on the first heating (plot 500). Such transitions do not generally have energy barriers to the ordering process and therefore show little or no hysteresis in the transition on reversal of the temperature change (unlike first order transitions which typically commence at significantly lower temperatures on cooling due to the presence of an energy barrier for the nucleation process). The present instance is, however, distorted by kinetic instability insofar as once the system has disordered completely and cooled down again, it does not exactly repeat itself on the next cycle. Rather the disordering is not as sharp and the heat capacity peak is postponed to higher temperature.

Figure 6:
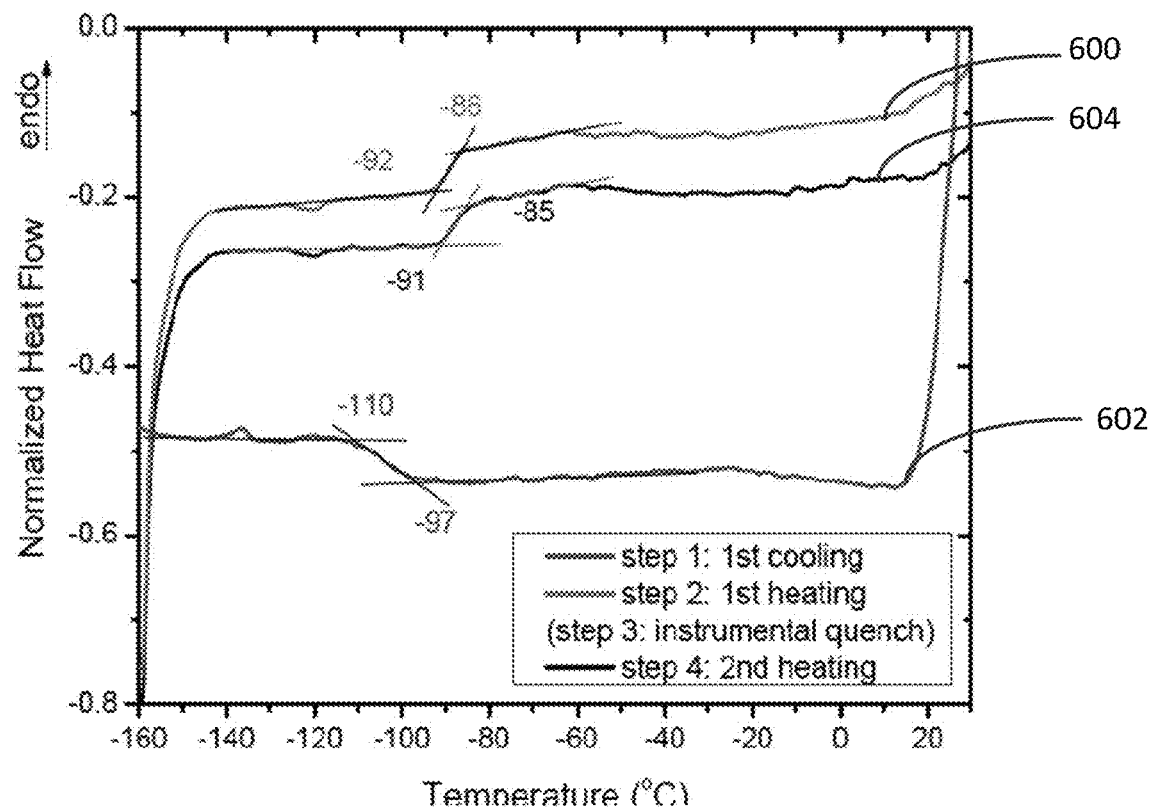
FIG. 6 shows repeat low temperature DSC scans taken three days after those of FIG. 4.

Samples that have been maintained at temperatures not exceeding room temperature (25° C.) seem to be less prone to loss of their character. This is exemplified by the repeat heating and cooling runs of FIG. 6, in which plots 600, 602, and 604 correspond to a first heating scan, a first cooling scan, and a second heating scan, respectively, of Li3 taken three days after those in FIG. 4. These repeat low temperature DSC scans indicate that the structure yielding the glass transition of FIG. 5 is stable over days of exposure to temperatures not exceeding room temperature. The "onset cooling" glass temperature in this sample, measured during the initial cooling (plot 602) is –97° C.

Figure 7:
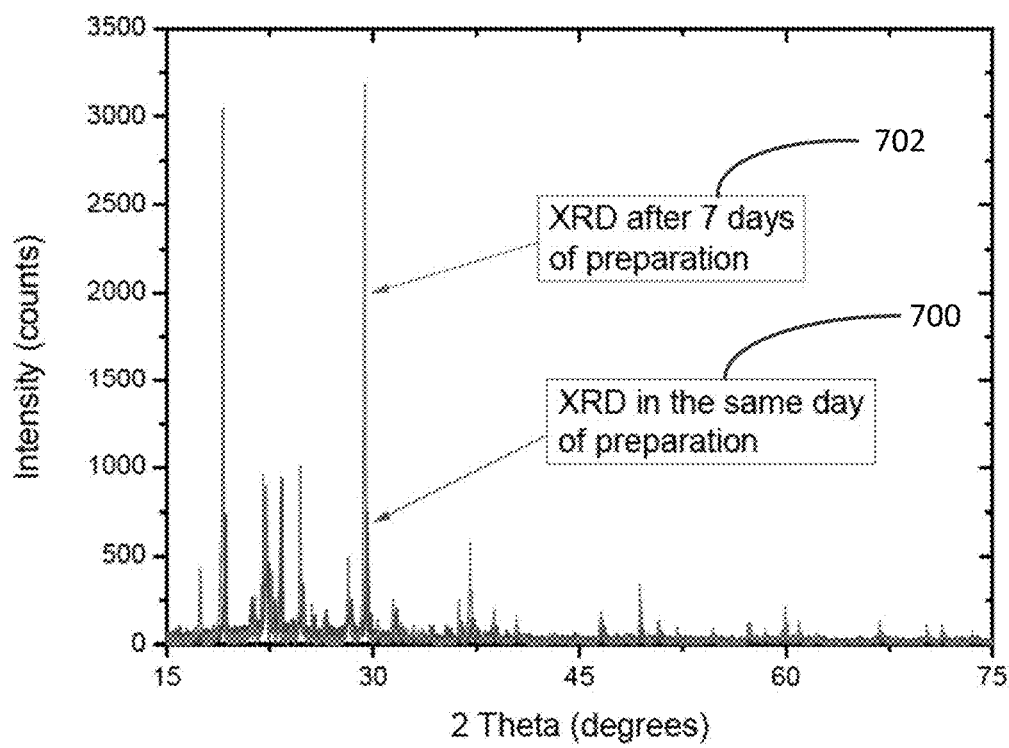
FIG. 7 shows an X-ray powder diffraction pattern for an alkali ion conducting plastic crystal electrolyte taken at different times after the initial preparation.

The crystalline nature of Li3 is shown by the X-ray powder diffraction patterns 700 and 702 of FIG. 7. Pattern 700 corresponds to Li3 on the day of sample preparation. Pattern 702 corresponds to the same sample seven days after preparation. The decrease in conductivity of Li3 over the course of several days appears to be associated with a change of structure to states of high crystallinity (e.g., growth of new and more ordered crystal structures with passing time) as indicated by the growth of intensity for some principal lines and the addition of new lines in X-ray pattern 702 compared to that of 700.

Figure 8:
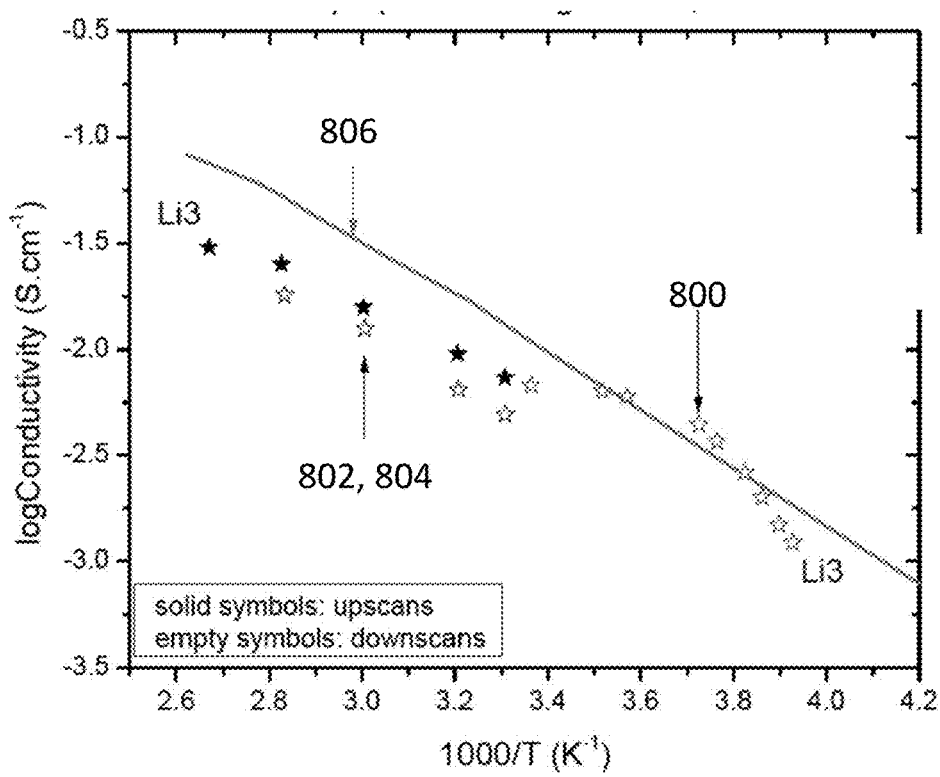
FIG. 8 shows conductivities for an alkali ion conducting plastic crystal electrolyte.

FIG. 8 shows conductivities for Li3 over a range of temperatures, with the data indicated by reference numbers 800 taken on the day of preparation and the data indicated by reference numbers 802 and 804 taken the following day. Reference number 804 indicates data from DSC upscans and reference numbers 800 and 802 indicate data from DSC downscans. Plot 806 shows an Arrhenius plot for the conductivity of the crystalline solid lithium ion conductor $Li_{10}GeP_2S_{12}$, taken from Kamaya et al., Nature Materials 10, 682 (2011). It makes a comparison with the conductivity of the standard lithium battery electrolyte $LiPF_6$ in molecular carbonate solvents, showing the low temperature conductivity of the $Li_{10}GeP_2S_{12}$. Based on this data, Li3 appears to maintain high conductivity at low temperatures.

Figure 9:
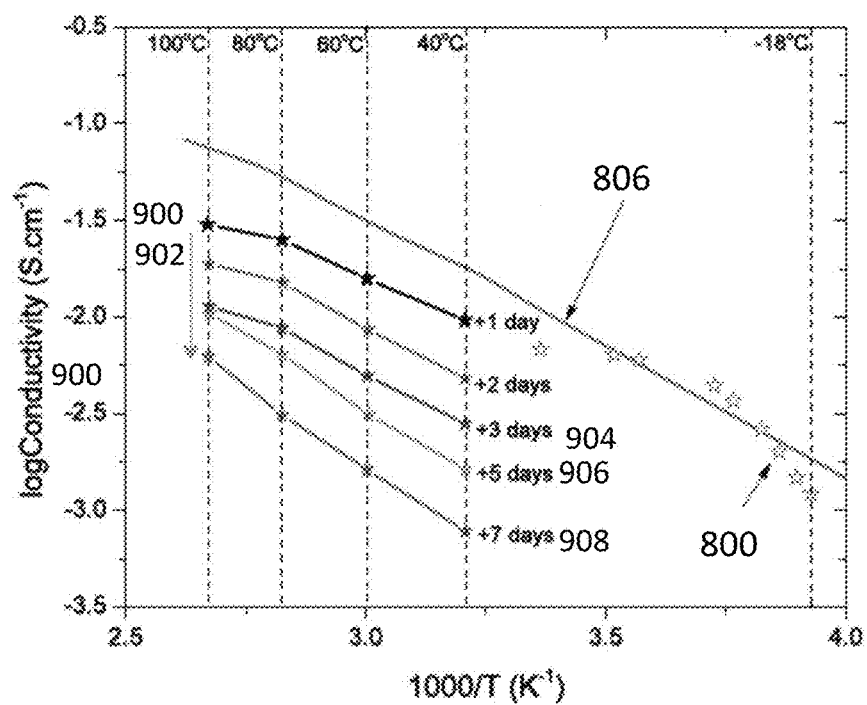
FIG. 9 shows a decrease in conductivity of an alkali ion conducting plastic crystal electrolyte over time.
Figure 10:
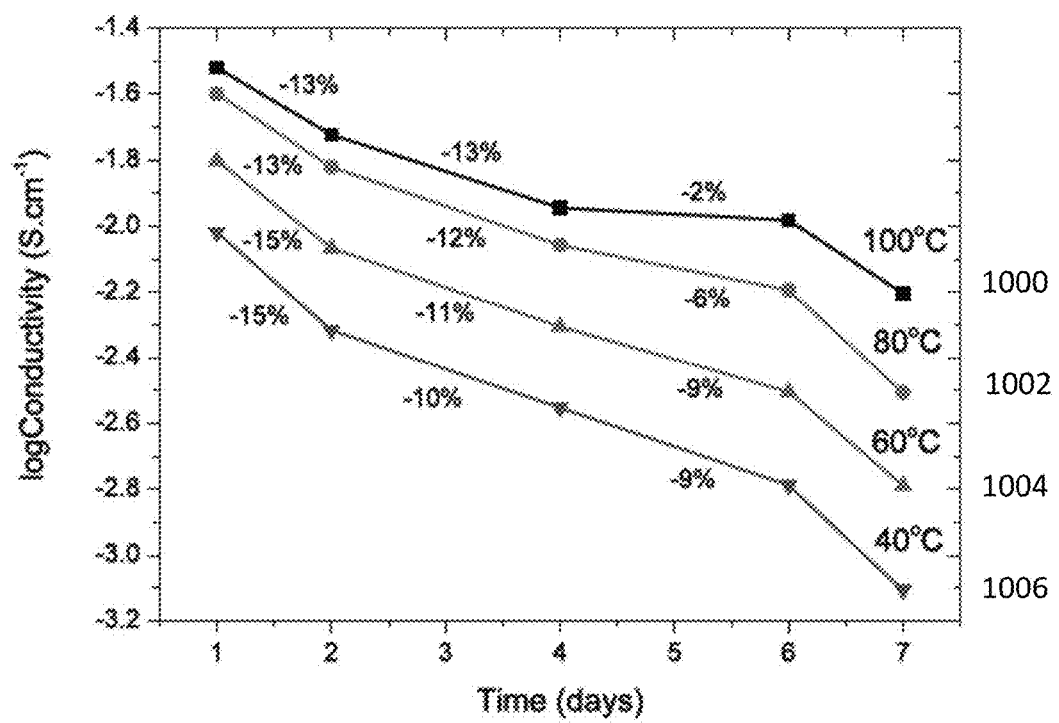
FIG. 10 shows time dependence of conductivity of an alkali ion conducting plastic crystal electrolyte at different temperatures.

FIG. 9 shows a decrease of Li3 sample conductivity with time, with plots 900, 902, 904, 906, and 908 corresponding to 1, 2, 3, 5, and 7 days after preparation, respectively. Data points 800 and plot 806 from FIG. 8 are included for reference. FIG. 10 shows the decrease in conductivity over time (up to 7 days after preparation) for Li3 for various temperatures, with plots 1000, 1002, 1004, and 1006 corresponding to 100° C., 80° C., 60° C., and 40° C., respectively.

Example 4: Li2:Li3 (50:50 Mixture)

The solids Li2 and Li3 were prepared as described in Examples 2 and 3, respectively, and mixed together in a ball mill in the absence of heating (e.g., without raising the temperature) for 1 hour to yield a homogenous, white solid. Mixing Li2 and Li3 lowers, by entropy of mixing, the chemical potential of the phase that tends to crystallize, thereby stabilizing the mixture compared to Li2 or Li3 alone. The mixture of Li2 and Li3 yields a plastic crystal electrolyte with conductivity as high as that of Li3 in its initial (un-aged) state.

Figure 11:
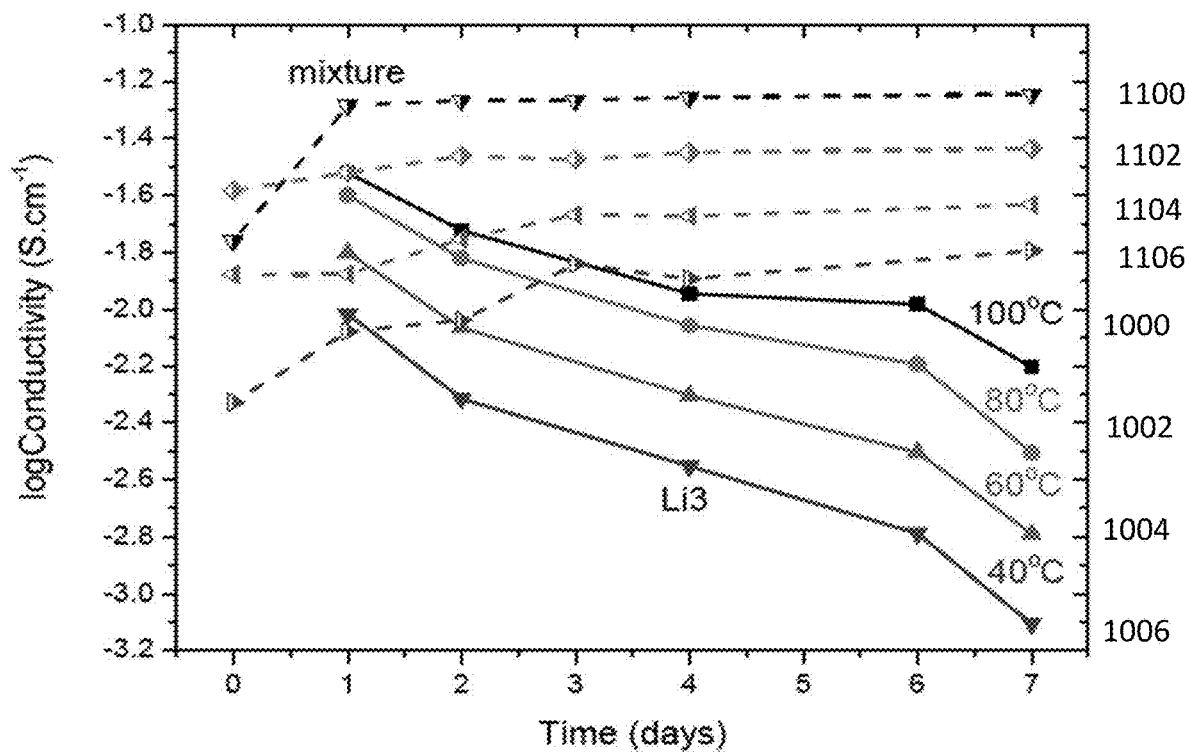
FIG. 11 shows a comparison of the time dependence of conductivity of the alkali ion conducting plastic crystal electrolyte of FIG. 10 and a mixture of alkali ion conducting plastic crystal electrolytes.

The subsequent stabilization of the system against deterioration, obtained by mixing of Li3 and Li2 compositions, is shown in FIG. 11, with plots 1000, 1002, 1004, and 1006 from FIG. 10 (Li3) for comparison, and plots 1100, 1102, 1104, and 1106 showing the time dependence of the conductivity of the Li2:Li3 (50:50) mixture at 100° C., 80° C., 60° C., and 40° C., respectively. As seen in FIG. 11, the conductivity is stabilized at values of 10-1.2 S/cm at 100° C. and 10-1.8 S/cm at 40° C. (~10-2 S/cm at ambient). After three days, the mixture conductivities have all stabilized at values that exceed their initial values. Even in the "aged" state, the conductivity remains high for a solid state conductor.

Example 5: Na2

The sodium analog of Li2 was prepared by a similar procedure, with a difference being the introduction of the alkali metal as the chloride which reacted with the sulfosilicic acid releasing HCl. The reaction using the amide in place of halide is more strongly driven, however, and was used in subsequent preparations. The conductivity of the product of reaction, thought to be $Na_2Si(SO_4)_2Cl_2$, was found to increase suddenly, as in a first order transition, from ~1 mS/cm at 60° C. to 100 mS/cm at 100° C., and then to remain in the high-conducting state during cooling to ambient.

Figure 12:
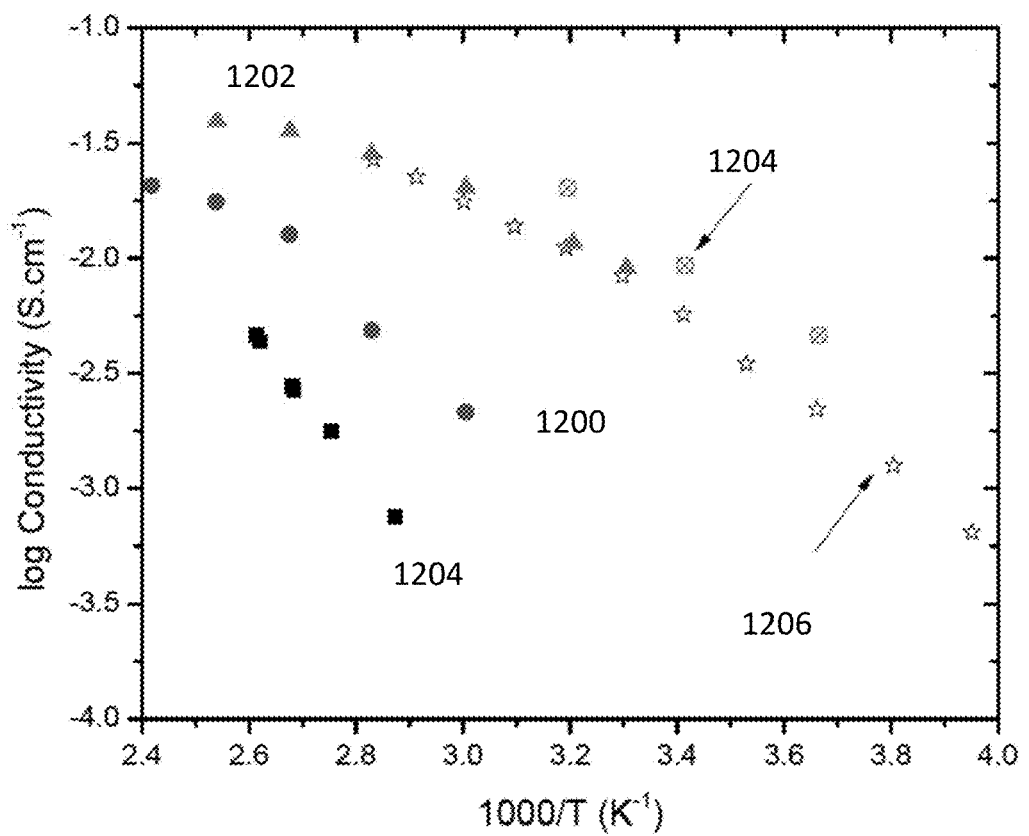
FIG. 12 is an Arrhenius plot of the ionic conductivity of three alkali ion conducting plastic crystal electrolytes and other electrolytes.

FIG. 12 is an Arrhenius plot, (i.e., a plot of the log (electrical conductivity) vs. reciprocal absolute temperature) for Li2 (solid circular data points labeled 1200), Li3 (solid triangular data points labeled 1202), and Li4 (solid square data points labeled 1204) prepared as described in Examples 1-3. Comparison is made with literature values for an ionic liquid polymer gel (Li bis(trifluoromethylsulfonyl)imide (LiTFSI)/1-ethyl-3-methylimidazolium bis(trifluoromethylsulfonyl)imide (EMIm TFSI), from Kim et al., J. Phys. Chem. 110, 16318 (2006), star data points labeled 1206), and the standard carbonate solvent electrolyte ($LiPF_6$/ethylene carbonate (EC)/dimethyl carbonate (DMC), from Tarascon et al., Solid State Ionics 69, 293 (1994), open circular data points with internal crosses labeled 1204).

Li2, Li3, and Li4 differ in the ratio of sulfuric acid to silicon in the initial acid production and consequently in the ratio of lithium to silicon in the final product. The data in FIG. 12 show that the Arrhenius equation commonly applicable to conductivity in crystalline or glassy materials does not give a good description of the conductors of the plastic crystal electrolytes described herein, though the curvature in the plots is smaller that of the molecular solvent (LiPF$_6$/EC/DMC as shown by 1208), or the ionic liquid gel polymer (LiTFSI/EMIm TFSI polymer electrolyte as shown by 1206). The lower curvature observed for Li2, Li3, and Li4 suggests that the low temperature conductivity of these electrolytes will remain high, unlike those of the molecular solvent and ionic liquid cases.

Preparation of Solid Acids and Solid Lithiated Compounds, for Compositions Li3 to Li1

As described below, a preference for formation of the fully sulfated silicosulfuric acid, i.e. Si(SO$_4$H)$_4$, rather than the compound most closely related to the initial composition stoichiometry, has been observed. This tetrasulfated formulation can be reliably formed using SiCl$_4$ as the starting material. For the other three, partially sulfated cases (Li1 through Li3), precursors are used in which there is a bulky group that is displaced from its silicon coordination much more rapidly than is the chlorine. The family of commercially available chlorophenylsilanes are examples of such precursors.

For each example described below, the stoichiometric (molar) amount of nominally anhydrous sulfuric acid was added to 1 mol of trichlorophenylsilane (to yield "H1"); or to dichlorodiphenylsilane (to yield "H2"); or to chlorotriphenylsilane (to yield "H3"). All of the reactions were carried out in 20 mL of dichloromethane and were kept at room temperature, closed, under nitrogen atmosphere and constant stirring for 24 hours. This yielded white waxy solids (yellow in the case of H3).

A stoichiometric amount of lithium amide was then added to each of the solid products, under nitrogen atmosphere and constant homogenization with an agate mortar and pestle. A slight excess of the amide (10 mol %) was subsequently added to ensure the completion of the reaction. The white powders resulting from H1, H2, and H3 are referred to herein as "Li1," "Li2," and "Li3," respectively.

Example 6: Li4

4 moles of nominally anhydrous sulfuric acid were added to 1.5 mol of silicon tetrachloride (i.e., a 50 mol % excess to ensure there would be no excess H$_2$SO$_4$) under nitrogen atmosphere. The mixture was kept in a closed system, comprised of a 3-neck Schlenk reaction flask, with a cold finger kept at around −20° C. and an internal HCl trap, kept in a separate tube connected to the Schlenk flask. The HCl trap is a liquid adduct formed by the mixture of 70 wt % of an equimolar diethylmethylamine-aluminum chloride adduct and 30 wt % of an equimolar 2-methylpyridine-aluminum chloride adduct.

The reaction mixture was kept at around 50° C. and stirred for 40 hours, yielding a colorless, transparent liquid (presumed to be the excess SiCl$_4$) and a white, gel-like solid. The solid was separated from the liquid by centrifugation for 2 hours and the excess liquid was evaporated by a continuous dry nitrogen gas flow. To obtain the lithium salt, 4 moles of lithium amide (LiNH$_2$) were gradually added to the solid product under nitrogen atmosphere with constant homogenization by means of an agate mortar and pestle. A slight excess of the amide (10 mol %) was subsequently added to ensure the completeness of the reaction. The resulting white powder is referred to herein as "Li4". The composition of Li4 is thought to be Li$_4$Si(SO$_4$)$_4$.

Example 7: Li3

3 moles of nominally anhydrous sulfuric acid were added to 1 mol of chlorotriphenylsilane, dissolved in 20 mL of dichloromethane, under nitrogen atmosphere. The mixture was kept at room temperature and stirred for 24 hours to yield a yellow waxy solid. 3 moles of lithium amide were then added to the solid product, under nitrogen atmosphere and constant homogenization with an agate mortar and pestle. A slight excess of the amide (10 mol %) was subsequently added to ensure the completion of the reaction. The resulting white powder is referred to herein as "Li3." It is believed that Li3 has a chemical formula of Li3Si(SO$_4$)$_3$Cl.

Example 8: Li2

2 moles of nominally anhydrous sulfuric acid were added to 1 mol of dichlorodiphenylsilane in 20 mL of dichloromethane under nitrogen atmosphere. The mixture was kept at room temperature and stirred for 24 hours to yield a white powder. 2 moles of lithium amide were then added to the solid product, under nitrogen atmosphere and constant homogenization with an agate mortar and pestle. A slight excess of the amide (10 mol %) was subsequently added to ensure the completion of the reaction. The resulting white powder is referred to herein as "Li2." It is believed that Li2 has a chemical formula of Li$_2$Si(SO$_4$)$_2$Cl$_2$.

Example 9: Li1

1 mol of nominally anhydrous sulfuric acid was added to 1 mol of trichlorophenylsilane in 20 mL of dichloromethane under nitrogen atmosphere. The mixture was kept at room temperature and stirred for 24 hours to yield a white waxy solid. 1 mol of lithium amide was then added to the solid product, under nitrogen atmosphere and constant homogenization with an agate mortar and pestle. A slight excess of the amide (10 mol %) was subsequently added to ensure the completion of the reaction. The resulting white powder is referred to herein as "Li1". It is believed that Li has a chemical formula of LiSi(SO$_4$)Cl$_3$.

Figure 13:
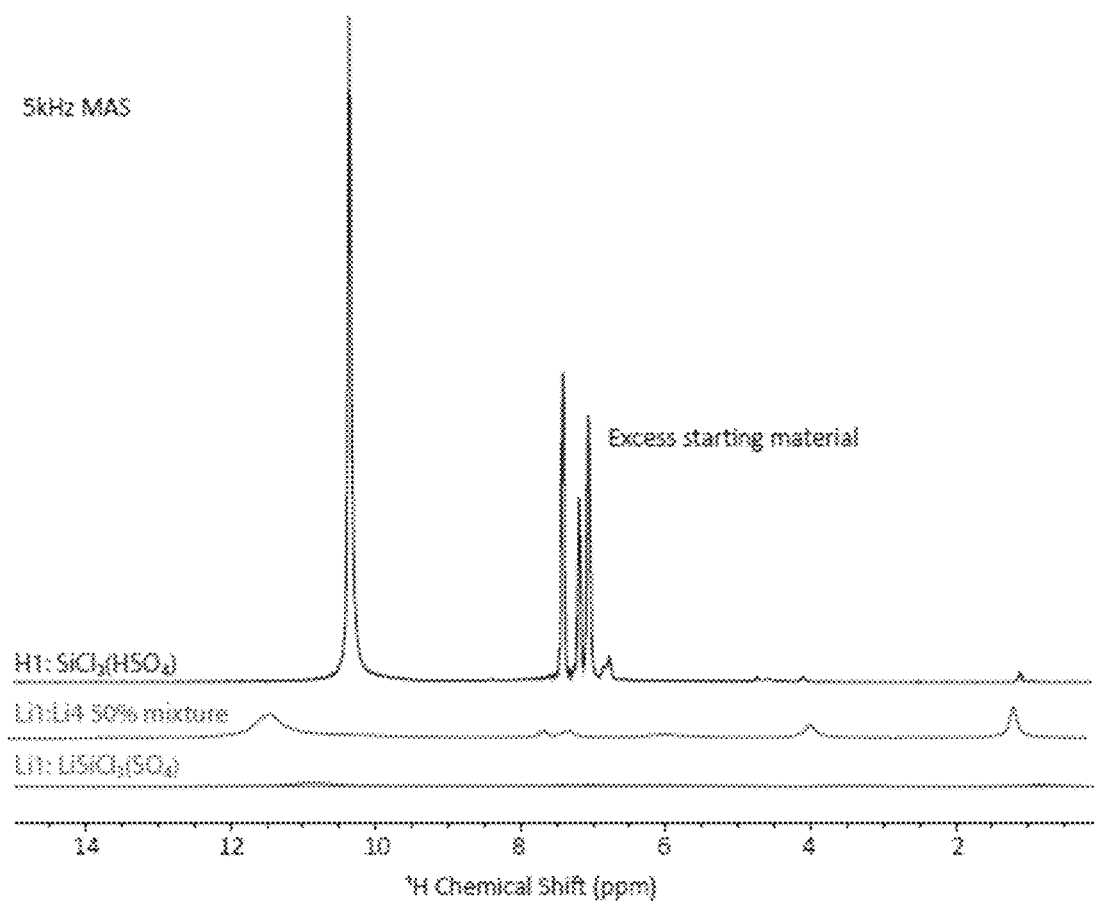
FIG. 13 shows $^1$H solid state magic angle spinning (MAS) NMR spectra of H1, Li1, and a 50 wt % mixture of Li1 and Li4 prepared as described herein.

FIG. 13 shows $^1$H NMR spectra of H1 (SiCl$_3$(HSO$_4$)) (upper trace), a 50% mixture by weight of Li1 and Li4 (LiSi(SO$_4$)Cl$_3$ and Li$_4$Si(SO$_4$)$_4$, respectively) (middle trace), and Li1 (LiSi(SO$_4$)Cl$_3$) (lower trace). The spike in the H1 spectrum (upper trace) is the pure H1 acid SiCl$_2$(HSO$_4$). The absence of this spike in the Li1:Li4 spectrum (middle trace) and Li1 spectrum (bottom trace) is understood to be related to neutralization of the acid with the lithium amide. The bottom trace, showing a substantial absence of protons in the neutralized H1 (i.e., Li1), indicates that conductivity measured from the compound is due exclusively or substantially exclusively to lithium ions. The middle trace, from the neutralization of the mixture of Li1 and Li4, shows trace amounts of unevaporated starting material and unreacted acid. The broad peaks indicate that the protons are relatively immobile.

Figure 14:
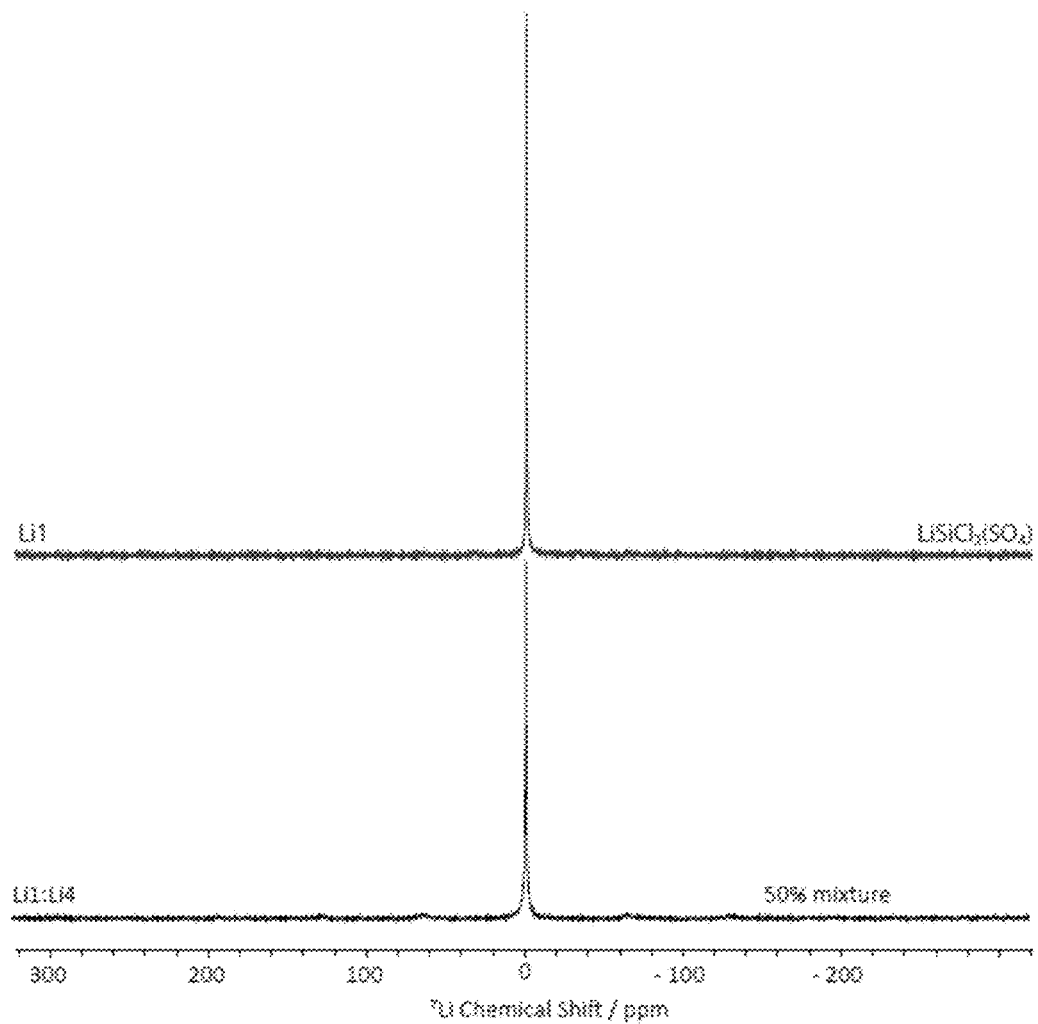
FIG. 14 shows $^7$Li solid state magic angle spinning (MAS) NMR spectra of Li1 and a 50 wt % mixture of Li1 and Li4 prepared as described herein.

FIG. 14 shows $^7$Li solid state magic angle spinning (MAS) NMR spectra of Li1 (upper trace) and a 50% mixture by weight of Li1 and Li4 (lower trace). Spinning side bands are absent in both spectra—an indication that the lithium atoms in both samples are highly mobile. Thus, these compounds, formed at room temperature, are expected to be excellent conductors.

Figure 15:
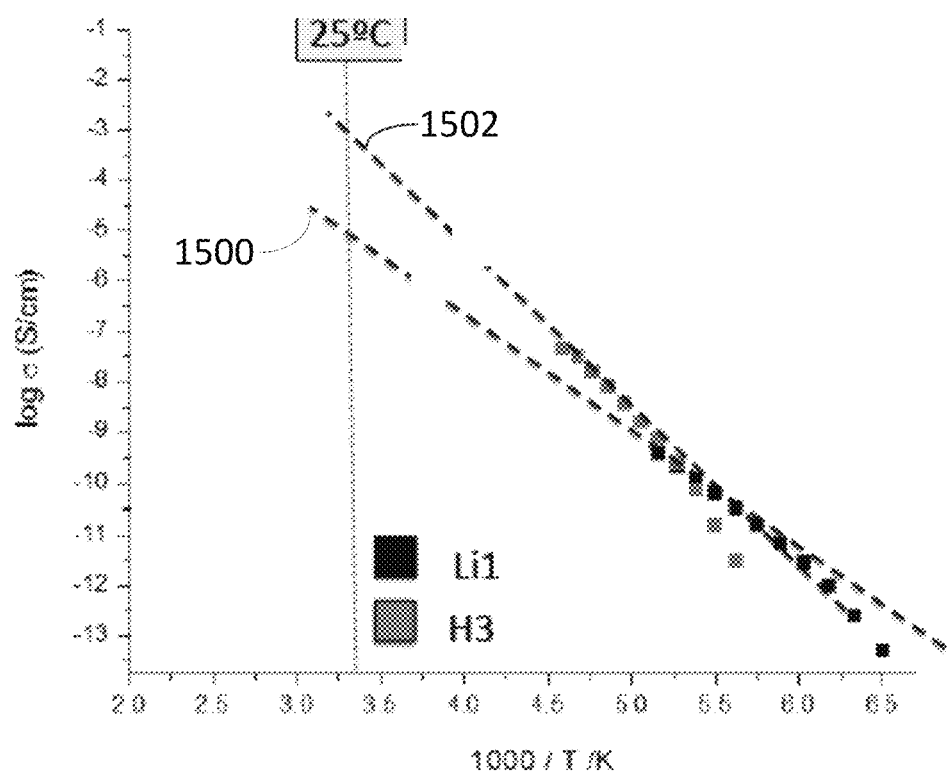
FIG. 15 shows conductivities for Li1 and H3 prepared as described herein, and measured by a technique that requires no electrode contact, but only works at low conductivities, which requires very low temperatures. In this temperature range the plastic phase has recrystallized to a less conductive form.

FIG. 15 shows low temperature conductivities for Li1 (plot 1500) and H3 (plot 1502) solid phases prepared as described herein, and in a more ordered and less conductive phase than that of the waxy material (plastic phase). This data was obtained with an "NMR tube" technique that requires no electrode contact, but only works at low conductivities, which requires very low temperatures. In this temperature range the plastic phase has recrystallized to a less conductive form.

Preparation of Exemplary Plastic Crystals

Example 10: $LiSi(CH_3)_3(SO_4)$ ("LiMethyl")

Trimethylphenylsilane (99%, Sigma-Aldrich) was added to sulfuric acid (99.999%, Sigma-Aldrich) in a 1:1 molar ratio under argon atmosphere (with slight excess of silane). The mixture was kept under constant stirring for 30 min. The final product was a yellow liquid. NMR: $^1H\delta=0.37$, 11.29 ppm; $^{13}C\delta=-0.67$ ppm; $^{29}Si\delta=37.34$ ppm. Lithium chloride was added to the liquid in a 1:1 molar ratio and left stirring for 48 hours under inert atmosphere by which time stirring action had been arrested by conversion to solid. Then the product was homogenized in an agate mortar and pestle, resulting in a soft waxy solid. For electrochemical cell measurements, using LiMethyl as electrolyte, the waxy solid was incorporated in Celgard 3401 by applying pressure with the mortar and pestle.

Example 11: $Si(OSO_3Li)_4$ (Li4)

Equally well-defined (by a single $^{29}Si$ MAS-NMR resonance) but less conductive, was the tetrasulfate. The reaction to obtain the precursor tetraprotic acid was performed in a closed system, comprised of a 3-neck Schlenk reaction flask. One of the joints contained a cold-finger maintained at a temperature of approximately ~−20° C. and another joint was attached to a tube containing an HCl trap. The HCl trap was a liquid mixture of two adducts: diethylmethylamine/aluminum chloride and 2-methylpyridine/aluminum chloride 70:30 in weight. Sulfuric acid (99.999%, Sigma-Aldrich) and silicon tetrachloride (99%, Sigma-Aldrich) were added to the Schlenk flask under argon atmosphere, in a molar ratio of 4:1. An excess of silicon tetrachloride was then added to ensure that no sulfuric acid would remain unreacted. The mixture was kept at room temperature for 24 hours with constant stirring. The constant evolution of bubbles from the mixture indicated the liberation of HCl gas. The final product was a white suspension, consisting of excess silicon tetrachloride and white solid H4 (confirmed by a single MAS $^{29}Si$-NMR peak at −118 ppm, and a ratio of S:Si ratio of 4.25:1 by ICP-OES). The H4 could be separated out by vacuum filtration, washing and drying. Conversion to the tetralithium salt was simply achieved by solid state reaction with lithium amide using a mortar and pestle to liberate ammonia and leave a white waxy solid.

Trimethoxyphenylsilane (97%, Sigma-Aldrich) was added to sulfuric acid (99.999%, Sigma-Aldrich) in a 1:1 mol ratio under argon atmosphere (with slight excess of silane). The mixture was kept under constant stirring for 30 min. The final product was a white, opaque solid and a colorless, transparent liquid, which was determined (via $^1H$ NMR) to be a mixture of benzene, methanol and starting silane. Lithium amide was added to the solid in a 1:1 molar ratio and homogeneized in an agate mortar and pestle, resulting in a soft waxy solid.

Example 12: $LiSi(OCH_3)_3(SO_4)$ ("LiMethox")

Trimethoxyphenylsilane (97%, Sigma-Aldrich) was added to sulfuric acid (99.999%, Sigma-Aldrich) in a 1:1 molar ratio under argon atmosphere (with slight excess of silane). The mixture was kept under constant stirring for 30 min. After decantation and washing of the resulting white solid with hexane, an excess of $LiNH_2$ was added to the solid and homogenized with a mortar and pestle. The final product, a mixture of $LiSi(OCH_3)_3(SO_4)$ and $LiSi(OCH_3)_2Ph(SO_4)$, according to $^{29}Si$ MAS-NMR studies is a white, waxy opaque solid. LiMethox may include from about 20 wt % to about 70 wt % of $LiSi(OCH_3)_3(SO_4)$ or 20 wt % to 70 wt % of $LiSi(OCH_3)_2Ph(SO_4)$, with the balance being about 80 wt % to about 30 wt % $LiSi(OCH_3)_2Ph(SO_4)$ or about 80 wt % to about 30 wt % $LiSi(OCH_3)_3(SO_4)$, respectively. In some cases, the molar ratio of $LiSi(OCH_3)_3(SO_4)$ to $LiSi(OCH_3)_2Ph(SO_4)$ is about 1:1.

Trimethylphenylsilane (99%, Sigma-Aldrich) was added to sulfuric acid (99.999%, Sigma-Aldrich) in a 1:1 mol ratio under argon atmosphere (with slight excess of silane). The mixture was kept under constant stirring for 30 min. The final product was a yellow liquid. NMR: $^1H\delta=0.37$, 11.29 ppm; $^{13}C\delta=-0.67$ ppm; $^{29}Si\delta=37.34$ ppm. Lithium amide was added to the liquid in a 1:1 molar ratio and left stirring for 48 hours under inert atmosphere. Then the product was homogenized in an agate mortar and pestle, resulting in a soft waxy solid. The waxy solid was incorporated in Celgard 3401 by applying pressure with the mortar and pestle. The neutralization step can also be performed using LiCl.

Example 13: $Li_3SiCl(SO_4)_3$ ("Li3")

Excess chlorotriphenylsilane was solubilized in 1,2-dichloroethane and added to sulfuric acid (99.999%, Sigma-Aldrich) in a 1:3 molar ratio under nitrogen atmosphere. The mixture was kept under constant stirring in an open vial for approximately 20 h. The final product was a transparent yellow solid (H3) in 1,2-DCE. The solvent was evaporated under gentle N2 flow and washed several times with dichloromethane. Finally, lithium amide 95% (Sigma-Aldrich) was added to the solid acid generating ammonia and the final soft solid, Li3.

Example 14: $LiSiCl_3(SO_4)$ ("Li1")

An attempt to prepare a material of this composition was made by adding excess trichlorophenylsilane (97%, Sigma-Aldrich) to sulfuric acid (99.999%, Sigma-Aldrich) in a 1:1 molar ratio under nitrogen atmosphere and stirring in an open vial for a period of some hours, which produced a white solid and a colorless, transparent liquid phase (benzene and excess starting silane, confirmed by $^1H$-NMR). The liquid phase was removed by decantation and vacuum evaporation, the solid acid was converted to the lithium equivalent by reaction with lithium amide until no more ammonia was evolved. When doubts about the product composition arose, a study of the evolution of the composition with time was made by a carrying out "chemical quenches" after different reaction times. The "quench" again involved addition of lithium amide to remove the unreacted protons. Different reaction times of 8 minutes, 32 minutes or 3 h30 minutes (the latter approximate) were used. The final product, a white solid in each case, was subjected to the $^{29}$Si MAS_NMR analysis. The analysis showed that displacement of Cl ligands did not stop when just a single phenyl group per molecule had been removed, as required to obtain the Li1 precursor composition. In fact, after only 8 min, the H1 and hence the Li1 silyl sulfate moiety was only a minority species, due to continued replacement of Cl ligands instead of the phenyl group displacements that had been anticipated from the reported high phenyl group lability.

Electrochemistry. Conductivity data were obtained by the standard complex impedance method. The electrochemical impedance spectra (EIS) were collected in a PARSTAT VMP2 using 10-100 mV sine amplitudes and a frequency range of 200 KHz to 10 Hz. The samples were carefully packed inside a homemade twin Pt electrode glass dip cell, under inert atmosphere. The cyclic voltammogram of Li1Li3 was obtained with a PARSTAT VMP2 at 1 mV/s. Under argon atmosphere, the sample was impregnated in Celgard and placed inside a stainless steel coin cell with Li foil anode and LiFePO$_4$ cathode purchased from MTI Corporation. The cyclic voltammogram of LiMethyl was obtained in a PARSTAT 2273 at 20 mV/s. The sample was impregnated in Celgard and placed inside a stainless steel coin cell with 2 Li foil electrodes, under argon atmosphere. The lithium ion transference numbers were obtained by the potentiostatic polarization method using a PARSTAT VMP2. The electrolytes were packed in coin cells with 2 lithium foil electrodes. First, an EIS was recorded with a 10 mV sine amplitude and immediately after that a DC polarization of 10 mV was applied to the cell. The current response was recorded for 1 h until the steady state was reached. Finally, another EIS with a sine amplitude of 10 mV was recorded. Then the transference number was calculated with the equation $$t_+ = \frac{I_{ss}(\Delta V - I_0 R_0)}{I_0(\Delta V - I_{ss} R_{ss})},$$

where $I_{ss}$ is me steady state current, $\Delta V$ is the DC bias, $I_0$ is the initial current, $R_0$ is the initial electrolyte resistance and $R_{ss}$ is the steady state electrolyte resistance.

Nuclear Magnetic Resonance Spectroscopy. The solid-state NMR data were obtained using a Bruker 400 MHz AVANCE III spectrometer equipped with a 4 mm double resonance broad-band magic angle spinning probe. $^1$H NMR data for the solid acid H1 and the lithiated version of it Li1, were collected by placing the corrosive materials into 50 μL Kel-F rotor inserts obtained from Bruker. Although using a rotor insert reduces the amount of sample in the active volume of the probe, it minimizes the risk of the probe being exposed to corrosive materials. $^1$H MAS NMR spectra of these materials were collected using a 4.0 μs π/2 pulse, a recycle delay of 15 seconds and 4 scans. All solid-state NMR spectra were collected with a MAS rate of 5 kHz, and the probe temperature maintained at 25° C. The $^1$H chemical shifts were externally referenced to TMS in the solid state using adamantane ($^1$Hδ=1.63 ppm).

Differential Scanning calorimetry. Measurements were made using a DSC-7, Perkin Elmer. The calibration was done immediately before the measurements by the two-point method with indium (melting point at 156.6° C.) and cyclohexane (solid-solid transition at 86.6° C.) as the references for high and low temperature regions, respectively. The samples were sealed in aluminum pans under nitrogen atmosphere and scanned at a rate of 20K/min under helium atmosphere.

Figure 16:
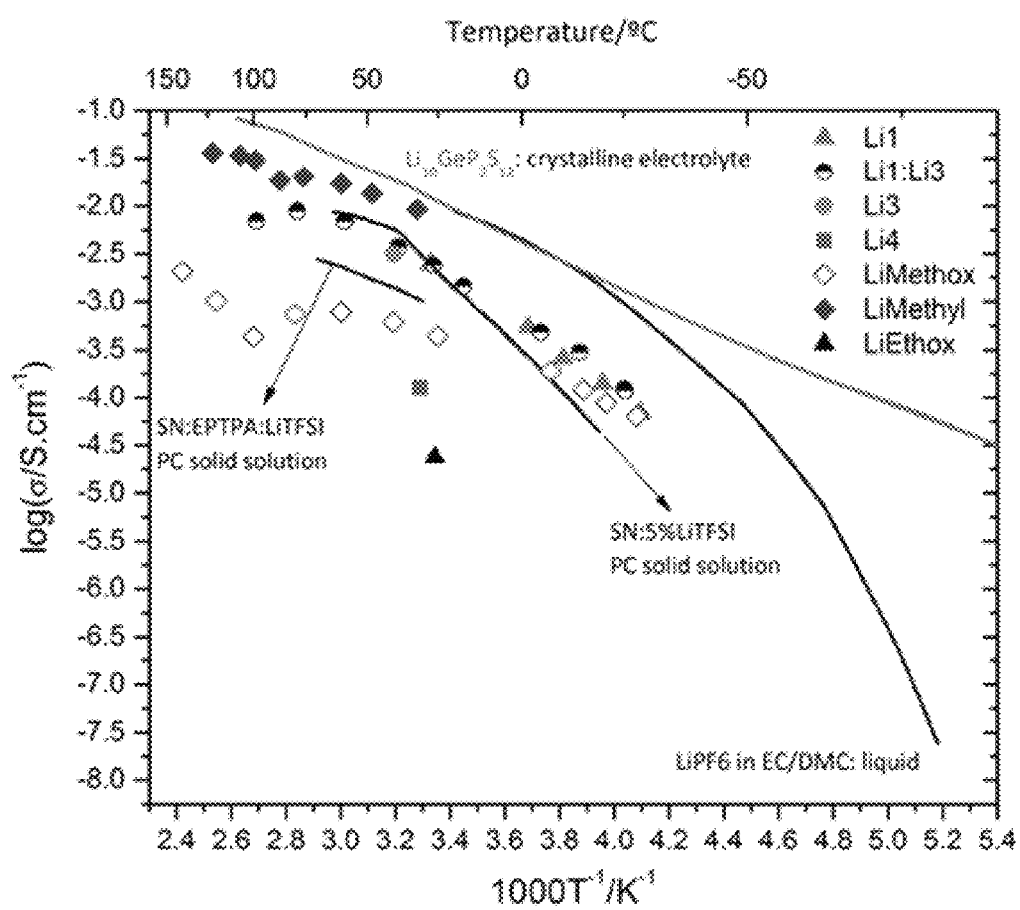
FIG. 16 shows Arrhenius plots of conductivities of the alkali ion conducting plastic crystals (colored squares) and select literature compounds.

The soft, white, waxy solids products have high conductivities as shown in the Arrhenius plot of FIG. 16. FIG. 16 shows Arrhenius plots of conductivities of the new solid state conductors (colored squares) and select literature compounds (solid lines): the crystalline Li$_{10}$GeP$_2$S$_{12}$; the standard electrolyte LiPF$_6$ in organic carbonates; and two solutions in plastic crystals. In the plastic crystals described herein, the ionic current is due substantially to Li$^+$. LiMe1 [(CH$_3$)$_3$SiSO$_4$Li] has high conductivity and is suitable for battery applications. The reaction mechanism involves the protonation (and subsequent elimination as benzene) of the phenyl groups in the silyl reagents.

Figure 17:
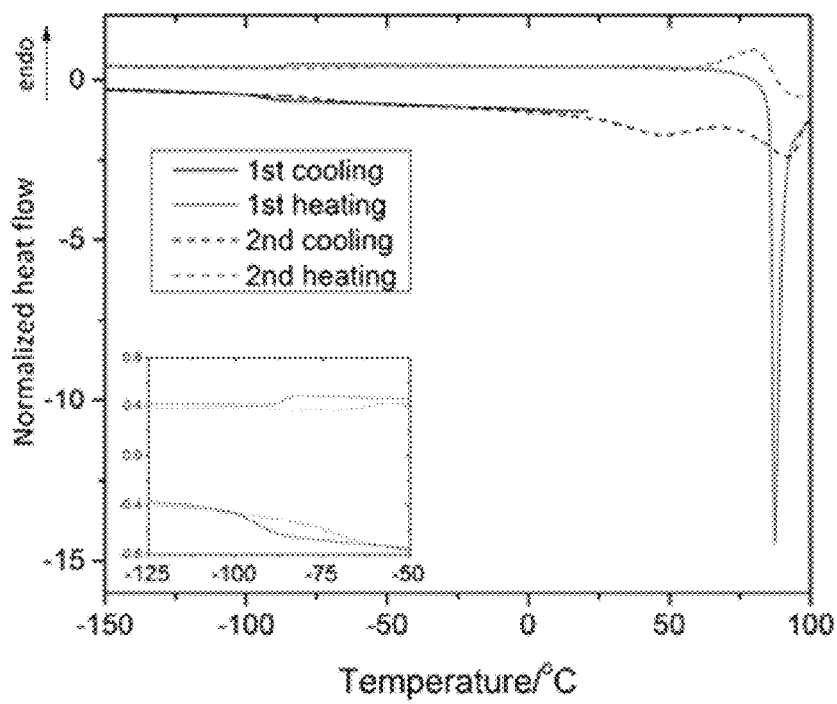
FIG. 17 shows differential scanning calorimetry data for Li1.

Although the soft, waxy lithium salts are highly conducting, they are prone to crystallization events that turn them into hard powders of low conductivity. The crystallization can happen suddenly on heating the sample to higher temperature (e.g., 90° C.), as seen in the DSC study of Li1 in FIG. 17, or just by letting the sample rest for 24 hours or more at ambient temperature. Before crystallization the materials exhibit a glass transition on cooling, and on reheating, at around −80° C. (see FIG. 17 and insert). On crystallization, the conductivity of the materials drops several orders of magnitude. FIG. 17 shows differential scanning calorimetry data for Li1. In the insert, bottom left, the $T_g$ is shown around −80° C. Note the ordering process that (during cooling) begins abruptly at 80° C. ends in a (cooling) glass transition at −80° C. as the rotational degrees of freedom are arrested in a glass transition. Not only is the crystallization (ordering) event irreversible, but the glass transition is suppressed after the first heating/cooling cycle. The crystallization of these waxy solids to an ordered, lower conducting phase may be suppressed by the principle of entropic stabilization of a homogeneous solution of a single phase. Stabilization of the plastic crystal form may be achieved by a mixture of separate preparations for Li4. The mixture of different preparations of Li4 may be effective in suppressing crystallization to the ordered, lower conducting phase because these different preparations may have different oligomeric components, preventing ordering of the solid. In these mixtures with varying oligomer content, the transition to an ordered phase has not been observed, thus maintaining the plastic crystal form and resultant high conductivities. One example of starting materials may be based upon mixed methylphenylsilanes (e.g., trimethylphenylsilane combined with dimethylphenylsilane).

Figure 18:
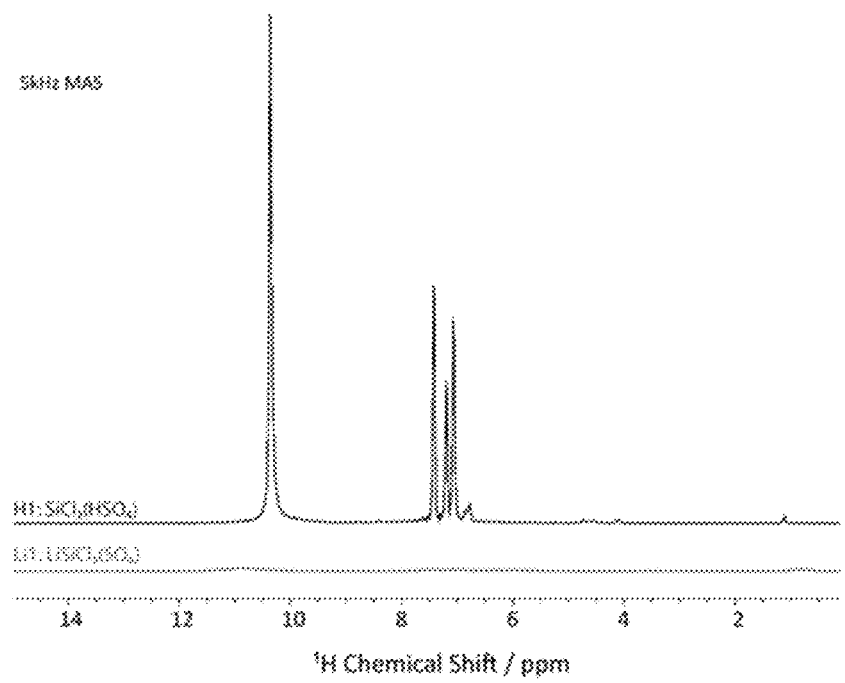
FIG. 18 shows NMR spectra of Li1 and its precursor.

FIG. 18 shows $^1$H MAS NMR spectra of the precursor (top) and Li1 (bottom), showing the lithiation process described herein suppresses the protons in the Li1 case and a majority of protons in the mixture case. The quantitative NMR experiment shows that, by using the phenyl group elimination for preparation of the precursor solid acid, the possibility of excess H$_2$SO$_4$ has been eliminated and, further, that a majority of the acidic protons can be neutralized by the reaction with lithium amide.

For battery applications, good contact between the electrolyte and the source of lithium ions, (lithium metal or alternative source such as Li(gr) or Li$_4$Si), and especially at the sink for the Li ions within the cathode of interest, is advantageous. LiCoO$_2$ cathodes were chosen for initial testing. Since the electrolyte is a soft solid, it may be forced into the micropores of a standard cell separator, such as Celgard. In one example, LiMethyl was used as the electrolyte. Sequestration in the Celgard micropores appeared to stabilize the high-conducting phase.

Micropores of the cell separator were filled in a low humidity glove box (<0.1 ppm $H_2O$ and <0.1 ppm $O_2$) by spreading the gel-like electrolyte on the cell separator surface (resting on the base of an agate mortar) and applying pressure with the pestle until the color of the initially white cell separator had transformed to a semi-transparent appearance, due to the reduction in light scattering from the originally empty pores. The lithium foil, electrolyte-filled cell separator, and cathode film were then pressed together in a button cell, which was sealed in the drybox environment, and then set in a vice to "cure" overnight.

Figure 19:
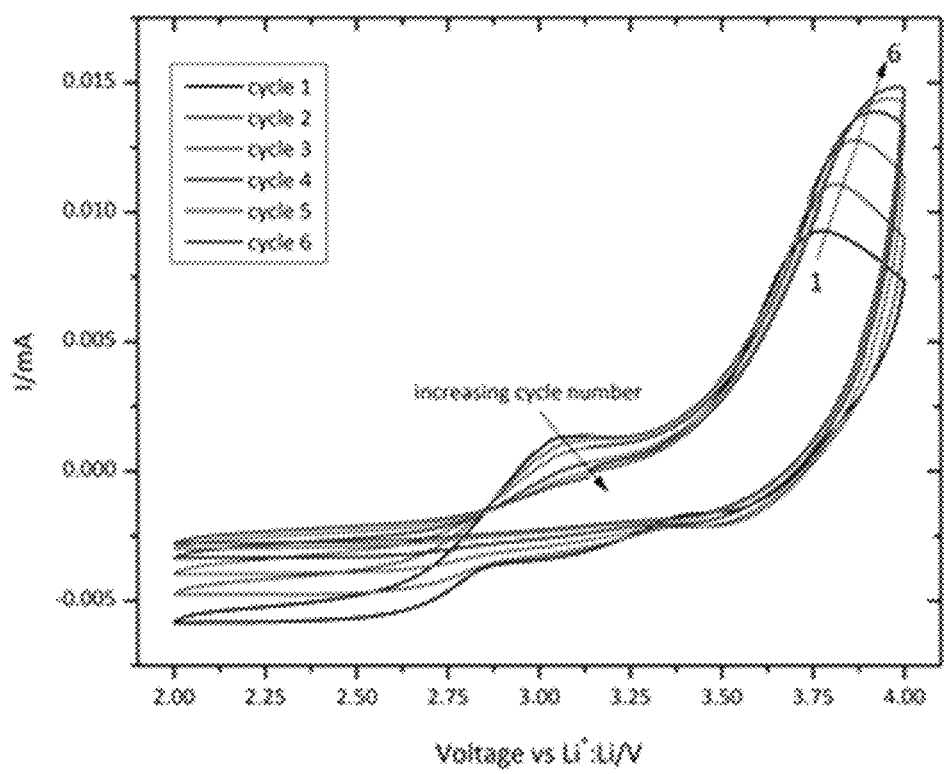
FIG. 19 shows cyclic voltammetry of a Li/Li1Li3/LiFePO$_4$ half cell.
Figure 20:
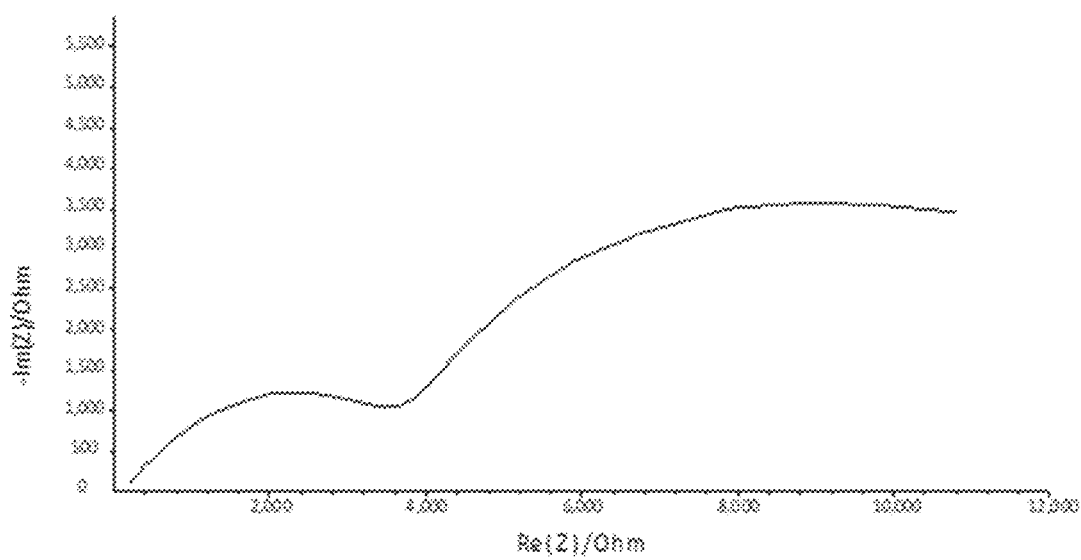
FIG. 20 shows an electrochemical impedance spectroscopy (EIS) spectrum of the Li/Li1Li3/LiFePO$_4$ half cell of FIG. 19.

Compounds described herein have been confirmed as suitable for solid state lithium-ion batteries by cyclic voltammetry using high voltage $LiCoO_2$ and $LiFePO_4$ cathodes. Coin cells were built using Li foil anodes and the LiMethyl and Li1:Li3 electrolytes incorporated in Celgard. The cyclic voltammograms show the reversible $Fe^{+3}/Fe^{+2}$ pair in the case of Li1:Li3 and $Co^{+3}/Co^{+2}$ pair in the case of LiMethyl for many cycles. FIG. 19 shows cyclic voltammograms of a Li/Li1Li3/LiFePO$_4$ half cell. FIG. 20 shows an electrochemical impedance spectroscopy (EIS) spectrum of the same cell. The cyclic voltammogram shows the lithium intercalation-deintercalation in the cathode at 3.5 V vs Li. With increasing cycle number, the current of the $Fe^{+2}/Fe^{+3}$ oxidation increases and the oxidation of the impurity at 3V decreases until it is substantially depleted by the 6$^{th}$ cycle. The EIS of the same cell is typical of an intercalation cathode/Li half cell.

Confirmation that the lithium ions are responsible for the high conductivities shown in FIG. 16 was obtained by lithium transference number measurements. The transference numbers were obtained by the usual impedance/DC polarization method for solid state electrolytes. The LiMethox compound yielded a transference number ~1.00.

Figure 21A:
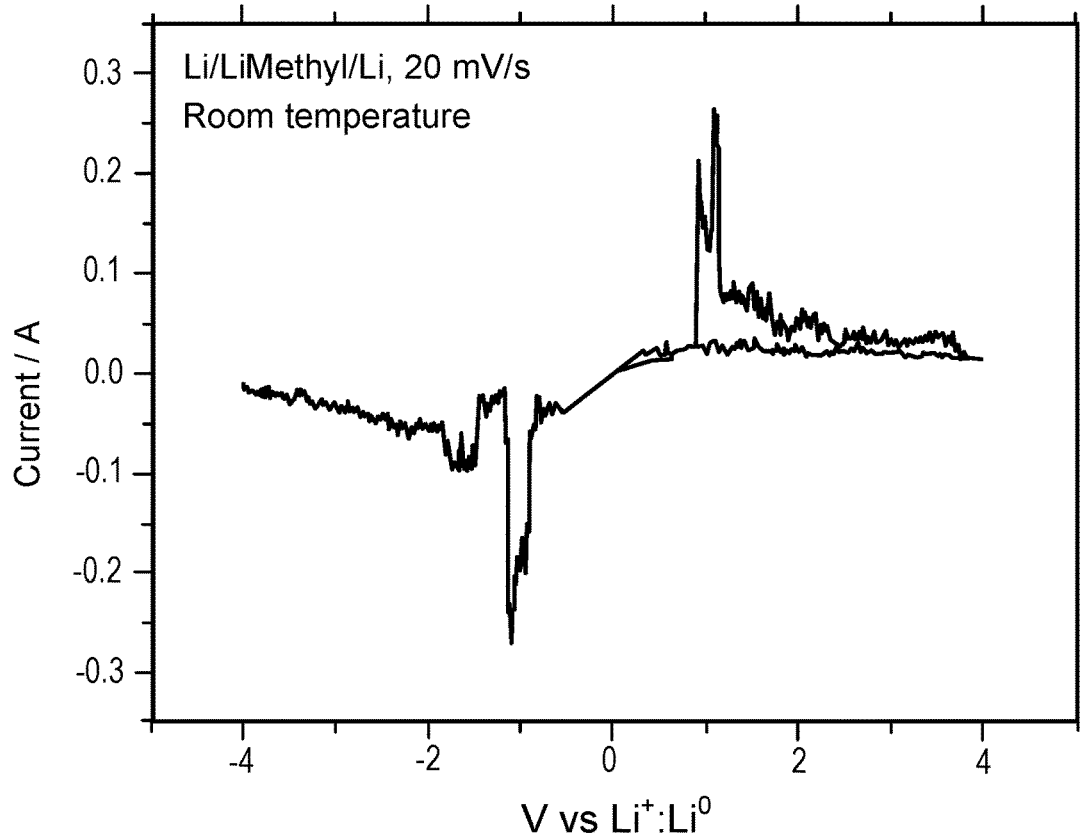
FIGS. 21A-21C show results of solid state electrochemistry experiments of a cell including LiMethyl incorporated in a Celgard separator.
Figure 21B:
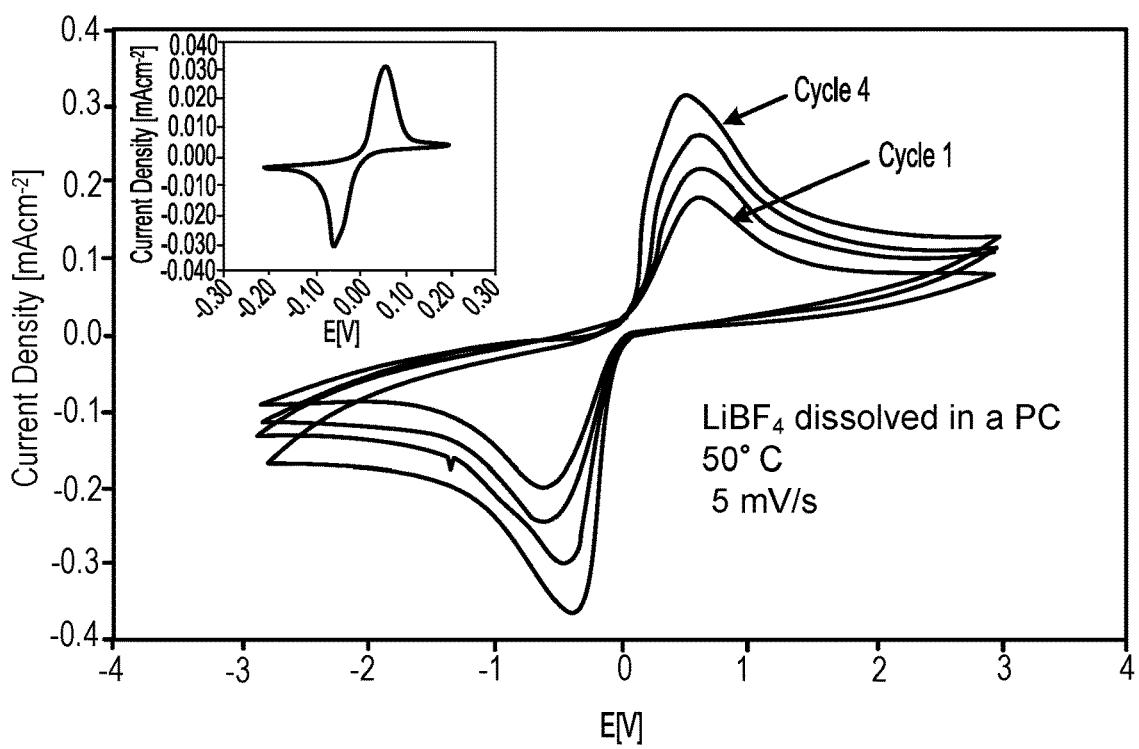
Figure 21C:
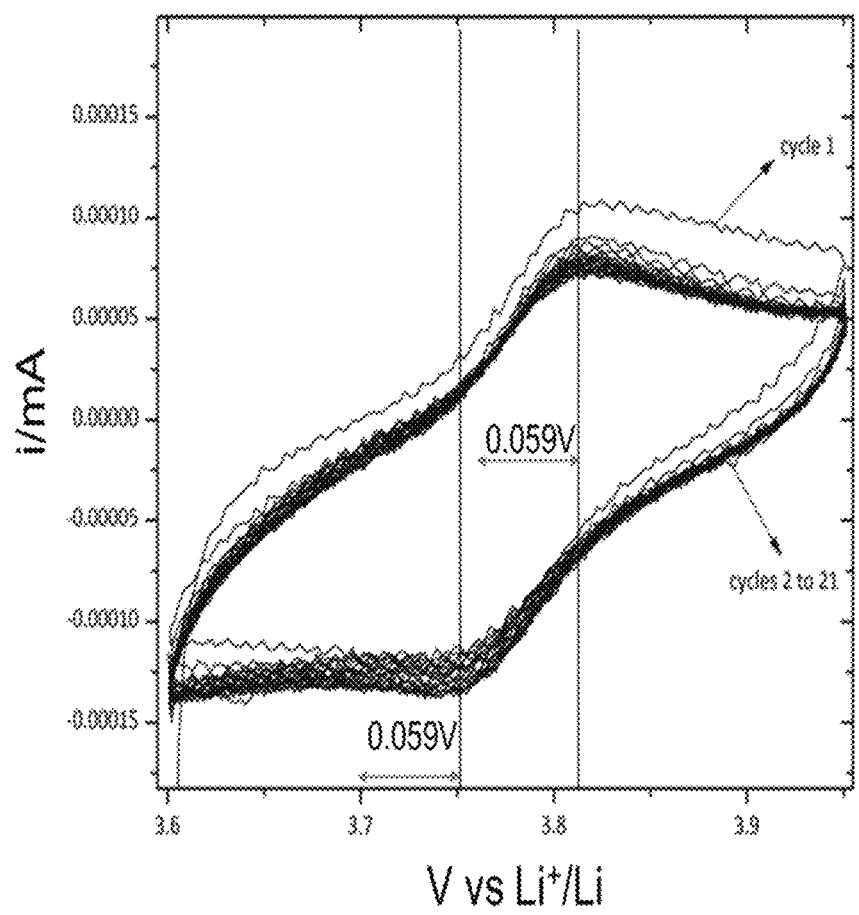

A lithium stripping/deposition plot for the latter cell was obtained using a different potentiostat that allowed for currents of the order of 1 A, and is shown in FIG. 20. FIGS. 21A-21C show all solid state electrochemistry experiments of the LiMethyl electrolyte, incorporated in Celgard 3401. FIG. 21A shows lithium stripping/deposition at 20 mV/s of the LiMethyl electrolyte, obtained in a symmetrical Li/Li coin cell. Note the very high currents. FIG. 21B shows LiBF$_4$ (10 mol %) dissolved in a N-ethyl-N-methylpyrrolidinium tetrafluoroborate plastic crystal from literature. FIG. 21C shows Li/LiMethyl/LiCoO$_2$ half cell showing lithium insertion through the $Co^{+3}/Co^{+2}$ pair, reversibly around 3.8 V. The peak to peak separation represents the difference between the oxidation and reduction steps. Of note is the small peak to peak separation in FIG. 21C, approaching the true reversibility value of 0.059 V. A value of 0.063 V is rarely obtained. The currents obtained are high, especially considering that this system is an all solid state cell. No $H^+/H_2$ pair was detected from the lithium stripping/deposition experiment, which again demonstrates that the lithiation was successful.

Figure 22:
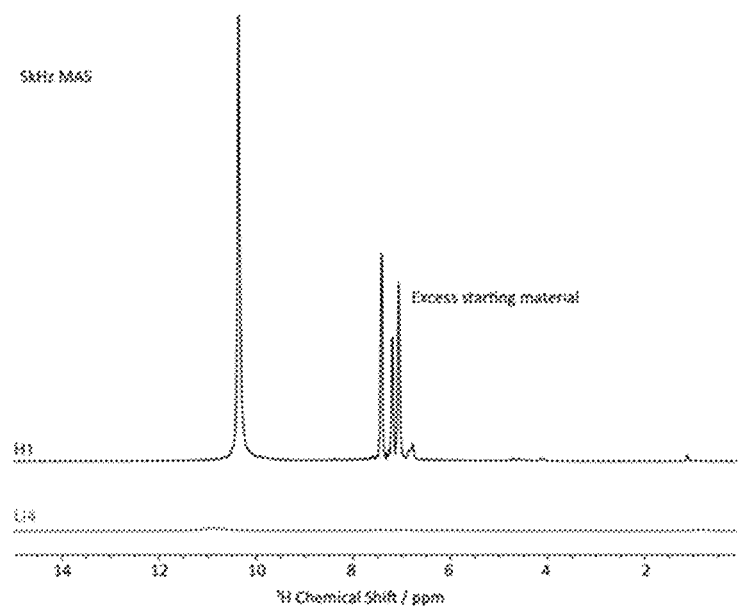
FIG. 22 shows $^1$H MAS NMR spectra of Li4 and its precursor.

FIG. 22 shows $^1H$ magic angle spinning (MAS) NMR spectra of Li4 and its precursor solid acid (H4, Si(SO$_4$H)$_4$), showing near quantitative removal of protons from the material.

Figure 23:
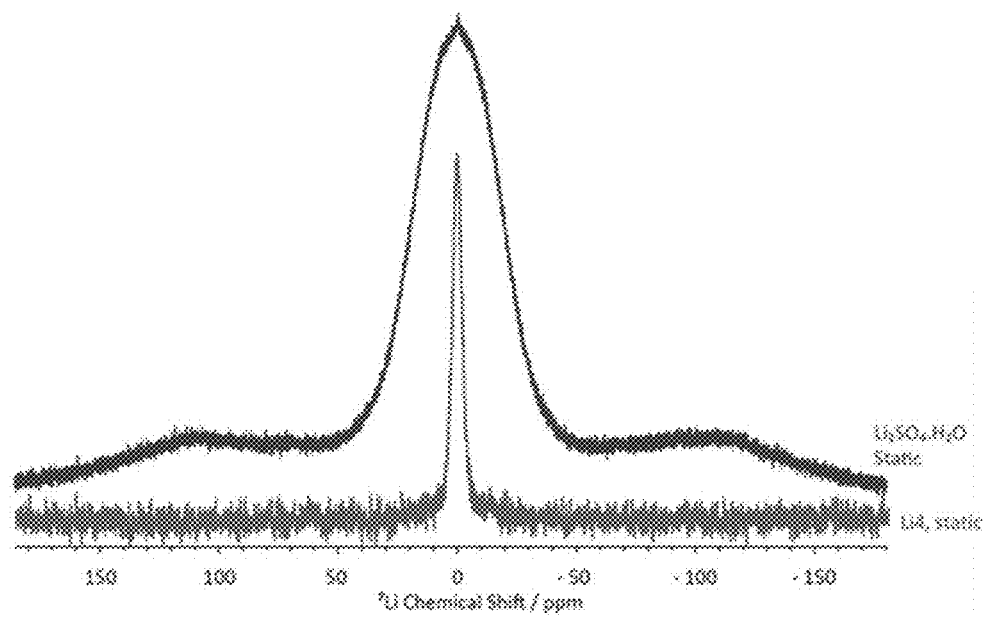
FIG. 23 shows static, solid state $^7$Li NMR spectra for Li4 and Li$_2$SO$_4$ hydrate.

FIG. 23 shows static, solid state $^7Li$ NMR spectra of Li4 and $Li_2SO_4$ hydrate. Lithium sulfate becomes a plastic crystal at high temperature (about 600° C.); below that temperature, it is not ionically conductive. The considerably sharper static lineshape of Li4 relative to $Li_2SO_4$ is consistent with a motional averaging of the quadrupolar moment of the $^7Li$ nuclei. This indicates that the lithium atoms of Li4 are in a relatively dynamic local environment, which is consistent with the high conductivity seen in the Arrhenius plot in FIG. 16.

Figure 24:
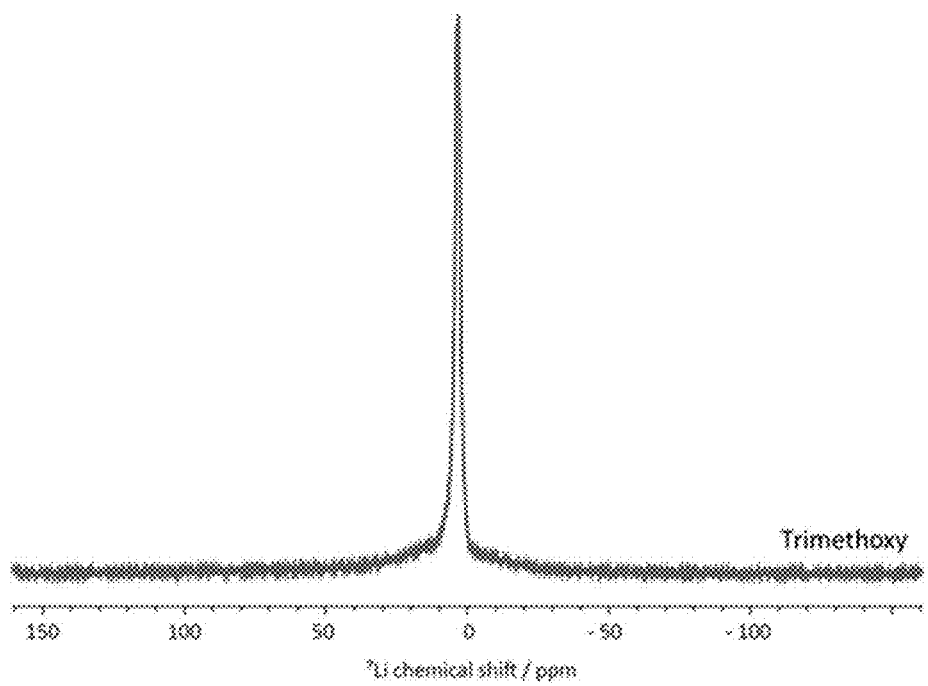
FIG. 24 shows a static, solid state $^7$Li NMR spectrum of LiMethox.

FIG. 24 shows static, solid state $^7Li$ NMR of LiMethox. The sharp line in this static spectrum indicates the high level of fast dynamic disorder of the Li ions and their environment, leading to motional narrowing of the $^7Li$ spectrum in this plastic crystal.

A number of embodiments of the invention have been described. Nevertheless, it will be understood that various modifications may be made without departing from the spirit and scope of the invention. Accordingly, other embodiments are within the scope of the following claims.

What is claimed is:

1. A solid electrolyte represented by general formula Li$_y$SiR$_x$(MO$_4$)$_y$, wherein:
   x is an integer from 1 to 3 inclusive,
   y=4–Z,
   each R present is independently C1-C2 alkoxy, and
   M is sulfur or selenium.

2. The solid electrolyte of claim 1, wherein each R present is independently C1-C2 alkoxy.

3. The solid electrolyte of claim 2, wherein at least one R is methoxy.

4. The solid electrolyte of claim 2, wherein at least one R is ethoxy.

5. The solid electrolyte of claim 1, wherein x is 1.

6. The solid electrolyte of claim 1, wherein x is 2.

7. The solid electrolyte of claim 1, wherein x is 3.

8. A composition comprising a mixture of two or more different solid electrolytes of claim 1.

9. A method of making a solid electrolyte, the method comprising:
   combining a phenylsilane and a first acid to yield a mixture comprising benzene and a second acid, wherein the phenylsilane comprises at least one C1-C3 alkyl substituent or at least one C1-C2 alkoxy substituent and the first acid comprises a diprotic acid;
   combining at least one of an alkali halide, an alkali amide, or an alkali alkoxide with the second acid to yield a product comprising a solid electrolyte represented by general formula Li$_y$SiR$_x$(MO$_4$)$_y$, wherein:
   x is an integer from 1 to 3 inclusive, y=4–X,
   each R present is independently C1-C2 alkoxy, and
   M is sulfur or selenium.

10. The method of claim 9, wherein the phenylsilane is selected from the group consisting of trimethylphenylsilane, trimethoxyphenylsilane, methyldiethylphenylsilane, dimethylethylphenylsilane, diphenyldimethylsilane, dimethyldiphenylsilane, monomethyltriphenylsilane, triethylphenylsilane, methyldimethoxyphenylsilane, dimethylmethoxyphenylsilane, dimethylethoxyphenylsilane, methyldiethoxyphenylsilane, methylmethoxyethoxyphenylsilane, ethylmethoxyethoxyphenylsilane, triethoxyphenylsilane, methylethylpropylphenylsilane, methyldipropylphenylsilane, ethyldipropylphenylsilane, methypropyldiphenylsilane, methylpropyldiphenylsilane, ethylpropyldiphenylsilane, methylethylpropoxyphenylsilane, methyldipropoxyphenylsilane, dipropoxydiphenylsilane, methylethoxypropoxyphenylsilane, and ethoxypropoxydiphenylsilane.

11. The method of claim 9, wherein the alkali amide is selected from the group consisting of lithium amides, sodium amides, and potassium amides.

12. The method of claim 9, wherein the alkali alkoxide is selected from the group consisting of lithium alkoxides, sodium alkoxides, and potassium alkoxides.

13. The method of claim 9, wherein combining the phenylsilane and the first acid replaces a phenyl group of the phenylsilane with a hydrogen oxyacid group to yield a silane, and the oxyacid group comprises sulfate or selenite.

14. The method of claim 9, wherein the solid electrolyte is a first solid electrolyte, and further comprising combining the first solid electrolyte and a second solid electrolyte to yield a composite solid electrolyte.

15. The method of claim 9, wherein the diprotic acid comprises at least one of sulfuric acid or selenic acid.

16. The method of claim 9, wherein the alkali halide is selected from the group consisting of lithium halides, sodium halides, and potassium halides.

17. The method of claim 16, wherein the alkali halide is an alkali chloride.

18. The method of claim 9, wherein the second acid is in the form of a liquid or a solid.

19. The method of claim 9, wherein the product is in the form of a waxy solid.

* * * * *